US010395368B2

(12) United States Patent
Berezhna et al.

(10) Patent No.: US 10,395,368 B2
(45) Date of Patent: Aug. 27, 2019

(54) METHODS AND SYSTEMS FOR ASSESSING HISTOLOGICAL STAINS

(71) Applicant: Abbott Laboratories, Abbott Park, IL (US)

(72) Inventors: Svitlana Y. Berezhna, Los Gatos, CA (US); Rene Nieves Alicea, San Francisco, CA (US); Marilou L. Coleman, Newark, CA (US); Walter G. Stonas, Campbell, CA (US); Willie J. Cowart, San Francisco, CA (US); Wenjing Li, Sunnyvale, CA (US); Ema C. Olah, Ventura, CA (US)

(73) Assignee: Abbott Laboratories, Abbott Park, IL (US)

( * ) Notice: Subject to any disclaimer, the term of this patent is extended or adjusted under 35 U.S.C. 154(b) by 34 days.

(21) Appl. No.: 15/378,495

(22) Filed: Dec. 14, 2016

(65) Prior Publication Data
US 2017/0178361 A1 Jun. 22, 2017

Related U.S. Application Data

(60) Provisional application No. 62/269,543, filed on Dec. 18, 2015.

(51) Int. Cl.
G06K 9/00 (2006.01)
G06K 9/32 (2006.01)
(Continued)

(52) U.S. Cl.
CPC ....... *G06T 7/0014* (2013.01); *G01N 15/1475* (2013.01); *G01N 33/52* (2013.01);
(Continued)

(58) Field of Classification Search
CPC ... G01N 15/1475; G06K 9/00127; G06T 7/90
See application file for complete search history.

(56) References Cited

U.S. PATENT DOCUMENTS 6,151,405 A * 11/2000 Douglass ........... G01N 15/1475
356/39
6,690,817 B1 * 2/2004 Cabib ................ G01B 11/0675
382/134
(Continued)

FOREIGN PATENT DOCUMENTS

WO 2006/036411 4/2006

OTHER PUBLICATIONS

Pham et al., "Quantitative image analysis of immunohistochemical stains using CMYK color model", Diagnostic Pathology 2007, 2:8, Feb. 27, 2007, pp. 1-10 (Year: 2007).*
(Continued)

*Primary Examiner* — Nay A Maung
*Assistant Examiner* — Jose Torres
(74) *Attorney, Agent, or Firm* — Edward J. Baba; Payal B. Sud; Bozicevic, Field & Francis LLP

(57) ABSTRACT

The present disclosure includes methods of assessing a histologically stained specimen based on a determined color signature of a region of interest of the specimen. Such assessments may be performed for a variety of purposes including but not limited to assessing the quality of the histological stain, as part of identifying one or more biologically relevant features of the image, as part of differentiating one feature of the image from other features of the image, identifying an anomalous area of the stained specimen, classifying cells of the specimen, etc. Also provided are systems configured for performing the disclosed methods and computer readable medium storing instructions for performing steps of the disclosed methods.

22 Claims, 8 Drawing Sheets

(51) Int. Cl.
  *G06K 9/46*      (2006.01)
  *G06K 9/62*      (2006.01)
  *G06T 7/00*      (2017.01)
  *G06T 7/90*      (2017.01)
  *G01N 15/14*     (2006.01)
  *G01N 33/52*     (2006.01)

(52) U.S. Cl.
  CPC ....... *G06K 9/0014* (2013.01); *G06K 9/00127* (2013.01); *G06K 9/00147* (2013.01); *G06K 9/3241* (2013.01); *G06K 9/4642* (2013.01); *G06K 9/4652* (2013.01); *G06K 9/6212* (2013.01); *G06T 7/90* (2017.01); *G06T 2207/10024* (2013.01); *G06T 2207/30024* (2013.01)

(56) References Cited

U.S. PATENT DOCUMENTS

| | | |
|---|---|---|
| 6,775,399 B1 | 8/2004 | Jiang |
| 9,011,773 B2 | 4/2015 | Shoffner et al. |
| 9,028,778 B2 | 5/2015 | Mamaghani et al. |
| 2003/0068076 A1* | 4/2003 | Torre-Bueno ........ G06K 9/0014 382/133 |
| 2005/0190966 A1 | 9/2005 | Etienne-Cummings et al. |
| 2010/0007727 A1* | 1/2010 | Torre-Bueno ...... G01N 21/6458 348/79 |
| 2010/0169024 A1 | 7/2010 | Madabhushi et al. |
| 2012/0263369 A1* | 10/2012 | Xie ....................... G06T 7/0012 382/134 |
| 2013/0137137 A1 | 5/2013 | Brody et al. |
| 2015/0293026 A1 | 10/2015 | Shin et al. |

OTHER PUBLICATIONS

Horobin & Walter (1987) "Understanding Romanowsky staining" Histochemistry 86:331-336.
Marshall et al. (1978) "Staining properties and stability of a standardised Romanowsky stain" J Clin Pathol 31(3):280-282.
Marshall et al. (1975) "A standardized Romanowsky stain prepared from purified dyes" J Clin Pathol 28(11):920-923.
Marshall et al. (1975) "An evaluation of some commercial Romanowsky stains" J Clin Pathol 28(8):680-685.

* cited by examiner

| Color | Red | Green | Blue | Red Coeff | Blue Coeff | B-R Balance |
|---|---|---|---|---|---|---|
| purple | 73 | 51 | 101 | 1.431373 | 1.383562 | 0.966598 |
| lavender | 126 | 138 | 187 | 0.913043 | 1.484127 | 1.625472 |
| deep blue | 7 | 56 | 162 | 0.125 | 23.14286 | 185.1429 |
| light blue | 4 | 136 | 192 | 0.029412 | 48 | 1632 |
| greyish blue | 76 | 123 | 168 | 0.617886 | 2.210526 | 3.577562 |
| turquoise | 77 | 191 | 183 | 0.403141 | 2.376623 | 5.895261 |
| green | 2 | 148 | 37 | 0.013514 | 18.5 | 1369 |
| yellow | 228 | 202 | 1 | 1.128713 | 0.004386 | 0.003886 |
| deep red | 193 | 44 | 27 | 4.386364 | 0.139896 | 0.031893 |
| raspberry | 201 | 84 | 83 | 2.392857 | 0.412935 | 0.17257 |
| pink | 206 | 93 | 149 | 2.215054 | 0.723301 | 0.326539 |

FIG. 4A
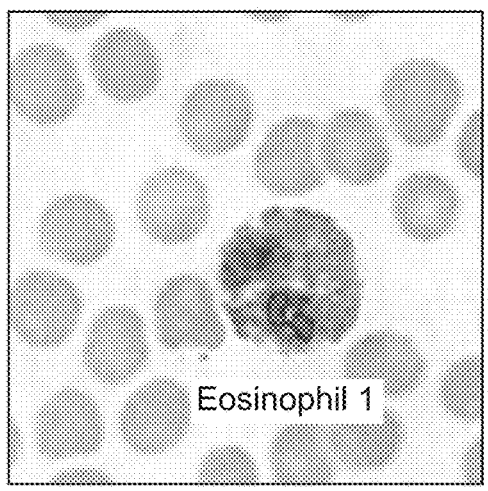 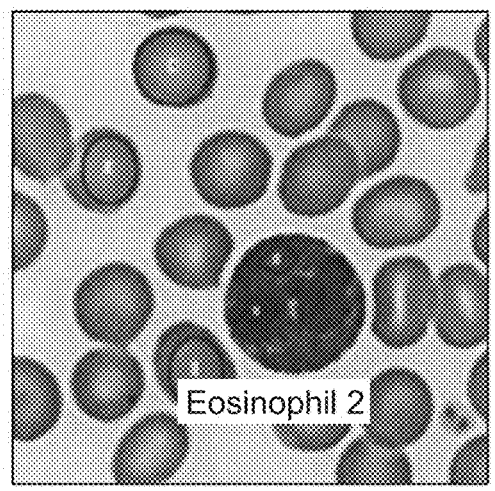
FIG. 4B
| Eosinophil 1 | Red | Green | Blue | Red Coeff | Blue Coeff | B-R Balance | Score |
|---|---|---|---|---|---|---|---|
| Nucleus | 96 | 111 | 191 | 0.864865 | 1.989583 | 2.300456 | 2 |
| Granules | 177 | 129 | 175 | 1.372093 | 0.988701 | 0.720578 | 3 |
| Eosinophil 2 | Red | Green | Blue | Red Coeff | Blue Coeff | B-R Balance | Score |
|---|---|---|---|---|---|---|---|
| Nucleus | 53 | 50 | 117 | 1.06 | 2.207547 | 2.082592 | 3.5 |
| Granules | 92 | 72 | 113 | 1.277778 | 1.228261 | 0.961248 | 3.4 |

| RBC-100%-Low | Red | Green | Blue | Red Coeff | Blue Coeff | B-R Balance | Score |
|---|---|---|---|---|---|---|---|
| Erythrocyte 1 | 171 | 155 | 157 | 1.103226 | 0.918129 | 0.832222 | 4 |
| Erythrocyte 2 | 168 | 153 | 157 | 1.098039 | 0.934524 | 0.851084 | 4 |
| Polychromatic | 155 | 150 | 166 | 1.033333 | 1.070968 | 1.03642 | |

| | Red | Green | Blue | Red Coeff | Blue Coeff | B-R Balance |
|---|---|---|---|---|---|---|
| Baso-15-Test | | | | | | |
| Nucleus | 67 | 67 | 151 | 1 | 2.253731 | 2.253731 |
| Granules | 50 | 51 | 129 | 0.980392 | 2.58 | 2.6316 |
| | | | | | | |
| Baso-1532-TH-Test | Red | Green | Blue | Red Coeff | Blue Coeff | B-R Balance |
| Nucleus | 106 | 87 | 165 | 1.218391 | 1.556604 | 1.27759 |
| Granules | 86 | 72 | 149 | 1.194444 | 1.732558 | 1.450514 |

**3D Scatterplot
Deep vs. Faint stain RGB values for
Lymphocytes nucleus**

METHODS AND SYSTEMS FOR ASSESSING HISTOLOGICAL STAINS

CROSS-REFERENCE

This application claims the benefit of U.S. Provisional Patent Application No. 62/269,543 filed Dec. 18, 2015, which application is incorporated herein by reference in its entirety.

INTRODUCTION

The assessment of histologically stained specimens, including the assessment of the quality of such specimens, is typically a very subjective endeavor. The methodology used in the field was established based on visual examination of the specimen under the microscope by one trained individual at time, when digital optical microscopy was not available yet. Currently applied methodology relies on human perception of coloration in different cell types and intracellular compartments, and includes distinguishing of various hues and intensities of colors. For example, for neutrophil granulocytes a desired cell coloration is described as "dark blue to purple nucleus, pale pink to almost colorless cytoplasm, red to lavender small granules". Similar type criteria (below provided) are used for all cell types. Not only is such description subjective in essence, the methodology is highly dependent on the spectral properties and intensity of the light source used for specimen illumination in the microscope. Per se, coloration of the same specimen observed in the microscope with halogen lamp illumination appears different when observed in a microscope with LED (light emitting diode) illumination. When performed by a human observer, there is no way to re-calibrate the coloration pattern in images created in microscopes using different illumination sources For consistency of specimen analysis, e.g., in diagnostics, the quality and reproducibility of coloration patterns generated in stained histological specimens are extremely important to maintain, given that abnormalities in cells biology are often decided based on coloration appearance. For example, toxic granulation refers to changes in granulocyte cells seen on examination of the peripheral blood film of patients with inflammatory conditions. They are commonly found in patients with sepsis. Toxic granulation is descried as dark violet coarse granules found in granulocytes, particularly neutrophils. If stain composition is not properly formulated or the stain is not properly used, it may create conditions in the cells in which the normal neutrophilic granules tend to overstain and appear as toxic granules.

Despite the existence of many analytical methods of determining stain components and their relative amount, purity, pH and other physicochemical properties of the reagents involved, these properties are not useful in determining their final quality and usability, primarily because these characteristic are related to the final stained product and not only the quality of the individual reagents used. Factors like the combination of reagents and staining methods used, as well as the variability of the specimens heavily influence the quality of the stain obtained and usability. Certification agencies, such as the Biological Stain Commission, continue to base stain certifications on subjective evaluations of stained specimens performed by expert individuals. Moreover, the processes of manufacturing stains or instruments that use stained specimens require standardized analytical methods that could objectively measure their quality and usability.

As mentioned, below is an example of a scoring guidance used by medical specialists in evaluating stain quality (taken from, Brown, Hematology Principles and Procedures, $6^{th}$ ed., 1993. Lea and Febiger, Philadelphia, p. 102-105; Carr and Rodak, Clinical Hematology Atlas, $3^{rd}$ Ed., 2009. Saunders Elsevier):

"Stain Quality:

For slide review and manual diff answer the question in the line "Stain Quality Acceptable?" using the pull down choice list. Answer "Yes" if stained cells appear according to the following:

Erythrocytes: pink to red-orange biconcave discoid forms (usually)

Lymphocytes: dark violet nucleus with medium blue cytoplasm

Monocytes: lobated nucleus, medium purple with light blue cytoplasm

Neutrophils; dark blue to purple nucleus (3 or more lobes), pale pink to almost colorless cytoplasm, red to lavender small granules Eosinophils bright red or reddish orange granules in pale pink cytoplasm, blue to blue-purple nucleus (multi-lobed)

Basophils: deep purple and violet black granules in pale blue or neutral cytoplasm, dark blue to purple nucleus (often bilobed)

Platelets: clearly demarcated blue violet-purple granules in light blue cytoplasm"

The above guidance clearly demonstrates the subjective nature of conventional stain quality evaluations.

SUMMARY

Aspects of the instant disclosure include a method of assessing a histologically stained specimen, the method comprising: obtaining a digital color image of the specimen; defining on the image a region of interest (ROI) based on a biological feature of the specimen; separating the digital color image into individual color channels; determining a color signature for the ROI, wherein the color signature comprises quantification of one or more color parameters over the ROI in one or more of the individual color channels; and comparing the determined color signature to a reference color signature that is specific to the biological feature and the histological stain to assess the histologically stained specimen.

In other aspects, the method includes wherein the image separating is performed after defining the ROI. In some aspects, the one or more color parameters include the mean intensity of an individual color channel. In some aspects, the color signature includes a color coefficient calculated by determining the ratio of the mean intensity value for a first color channel to the mean intensity value for a second color channel.

In other aspects, the method includes wherein the color signature includes a first color coefficient calculated by determining the ratio of the mean intensity value for a first color channel to the mean intensity value for a second color channel and a second color coefficient calculated by determining the ratio of the mean intensity value for a third color channel to the mean intensity for the first or the second color channel.

In other aspects, the method includes wherein the color signature includes a third color coefficient calculated by determining the ratio of the first color coefficient to the second color coefficient.

In other aspects, the method includes wherein the ROI includes a cell or a portion thereof, a plurality of cells, the cytoplasm of a cell or a portion thereof or the nucleus of a cell or a portion thereof.

In some aspects, the reference color signature may be derived from a reference histologically stained specimen. In other aspects, the reference color signature includes a threshold value. In other aspects, the assessment includes establishing whether the determined color signature is within a predetermined range and, when within the range, the specimen is further processed. In other aspects, the assessment includes establishing whether the determined color signature is outside of a predetermined range and, when outside the range, the specimen is not further processed.

In other aspects, the method includes wherein the assessment is an evaluation of histological stain quality, the assessment is used in identifying the ROI as a feature of the image, the assessment is used in differentiating the ROI from other features of the image.

In other aspects, the method includes quantifying additional ROIs of the image having a substantially similar color signature.

In some aspects, the method includes wherein the histological specimen is stained with a Romanowsky stain.

In other aspects, the color signature includes a color coefficient calculated by determining the ratio of the mean intensity value for a red color channel to the mean intensity value for a green color channel and/or a color coefficient calculated by determining the ratio of the mean intensity value for a blue color channel to the mean intensity value for a red color channel. In some aspects, the color signature includes a first color coefficient calculated by determining the ratio of the mean intensity value for a red color channel to the mean intensity value for a green color channel and a second color coefficient calculated by determining the ratio of the mean intensity value for a blue color channel to the mean intensity value for a red color channel.

In other aspects, the method includes wherein the color signature includes a third color coefficient calculated by determining the ratio of the first color coefficient to the second color coefficient.

In other aspects, the histological specimen is derived from a biological sample including e.g., a blood sample, a bodily fluid sample or a tissue sample. In some aspects, the biological feature is a cell, wherein the cell includes e.g., an erythrocyte, a mast cell, a megakaryocyte, a basophil, a neutrophil, an eosinophil, a macrophage, a NK cell, a T cell, a B cell or a blood cell progenitor.

In some aspects, method includes a calibration of the illumination source used in obtaining the digital color image, wherein the calibration comprises quantification of one or more color parameters over an ROI defined on a blank slide.

Aspects of the instant disclosure include a method of assessing the quality of a histologically stained specimen, the method comprising: obtaining a digital color image of the specimen; defining on the image a region of interest (ROI) based on a biological feature of the specimen; determining a color signature for the ROI, wherein the color signature comprises quantification of one or more color parameters over the ROI; and comparing the determined color signature to a reference color signature that is specific to the biological feature and the histological stain to assess the quality of the histologically stained specimen.

In other aspects, the method includes wherein the one or more color parameters comprises optical density, hue, lightness and/or saturation. In some aspects the method includes separating the digital color image into individual color channels including e.g., wherein the separating is performed after defining the ROI.

In other aspects, the one or more color parameters include the mean intensity of an individual color channel. In some aspects, the color signature comprises two or more color parameters including e.g., optical density, hue, lightness, saturation and/or the mean intensity of an individual color channel.

In other aspects, the color signature comprises three or more color parameters including e.g., optical density, hue, lightness, saturation and/or the mean intensity of an individual color channel.

In other aspects, the ROI includes a cell or a portion thereof, a plurality of cells, the cytoplasm of a cell or a portion thereof and/or the nucleus of a cell or a portion thereof.

In other aspects, the color signature includes a cytoplasmic stain color vector (CSCV). In some aspects, the CSCV is determined based on red, green and blue color channels and is calculated according to the equation: $CSCV_{rgb} = \sqrt{(Mean_{red})^2 + (Mean_{green})^2 + (Mean_{blue})^2}$, wherein "Mean" represents the mean intensity value for each color channel over a ROI comprising the cytoplasm of a cell or a portion thereof. In other aspects, the CSCV comprises one or more directional components calculated according to the equation: $\beta_{CSCV_{rgb}} = \cos^{-1}(Mean_{blue}/CSCV_{rgb})$ or the equation: $\theta_{CSCV_{rgb}} = (\cos^{-1}(Mean_{red}))\sqrt{(Mean_{red})^2 + (Mean_{green})^2}$ or a combination thereof.

In other aspects, the cytoplasmic stain color vector is determined based on hue, saturation and luminosity values and is calculated according to the equation: $CSCV_{hsl} = \sqrt{(Mean_{hue})^2 + (Mean_{saturation})^2 + (Mean_{luminosity})^2}$, wherein "Mean" represents the mean hue, saturation and luminosity values over a ROI comprising the cytoplasm of a cell or a portion thereof. In some aspects, the CSCV comprises one or more directional components calculated according to the equation: $\beta_{CSCV_{hsl}} = \cos^{-1}(Mean_{lightness}/CSCV_{hsl})$ or the equation: $\theta_{CSCV_{hsl}} = (\cos^{-1}(Mean_{hue}))\sqrt{(Mean_{hue})^2 + (Mean_{saturation})^2}$ or a combination thereof.

In other aspects, the color signature comprises a nuclear stain color vector (NSCV). In some aspects, the nuclear stain color vector is determined based on red, green and blue color channels and is calculated according to the equation: $NSCV_{rgb} = \sqrt{(Mean_{red})^2 + (Mean_{green})^2 + (Mean_{blue})^2}$, wherein "Mean" represents the mean intensity value for each color channel over a ROI comprising the nucleus of a cell or a portion thereof. In some aspects, the NSCV comprises one or more directional components calculated according to the equation: $\beta_{NSCV_{rgb}} = \cos^{-1}(Mean_{blue}/NSCV_{rgb})$ or the equation: $\theta_{NSCV_{rgb}} = (\cos^{-1}(Mean_{red}))\sqrt{(Mean_{red})^2 + (Mean_{green})^2}$ or a combination thereof.

In other aspects, the nuclear stain color vector is determined based on hue, saturation and luminosity values and is calculated according to the equation: $NSCV_{hsl} = \sqrt{(Mean_{hue})^2 + (Mean_{saturation})^2 + (Mean_{luminosity})^2}$, wherein "Mean" represents the mean hue, saturation and luminosity values over a ROI comprising the nucleus of a cell or a portion thereof. In some aspects, the NSCV comprises one or more directional components calculated according to the equation: $\beta_{NSCV_{hsl}} = \cos^{-1}(Mean_{lightness}/NSCV_{hsl})$ or the equation: $\theta_{NSCV_{hsl}} = (\cos^{-1}(Mean_{hue}))\sqrt{(Mean_{hue})^2 + (Mean_{saturation})^2}$ or a combination thereof.

In other aspects, the color signature comprises the ratio of a cytoplasmic stain color vector to a nuclear stain color vector.

In other aspects, the reference color signature is derived from a reference histologically stained specimen. In some aspects, the reference color signature comprises a threshold value.

In other aspects, the assessment comprises establishing whether the determined color signature is within a predetermined quality range and, when within the range, the specimen is further processed. In some aspects, the assessment comprises establishing whether the determined color signature is outside of a predetermined quality range and, when outside the range, the specimen is not further processed.

In other aspects, the method includes wherein the histological specimen is stained with a Romanowsky stain. In some aspects, the histological specimen is derived from a biological sample including e.g., a blood sample, a bodily fluid sample or a tissue sample. In some aspects, the biological feature is a cell including e.g., an erythrocyte, a mast cell, a megakaryocyte, a basophil, a neutrophil, an eosinophil, a macrophage, a NK cell, a T cell, a B cell or a blood cell progenitor.

Aspects of the instant disclosure include a method of identifying an anomalous area of a hematological smeared specimen, the method comprising: obtaining a digital color image of the specimen; defining on the image a region of interest (ROI) spanning at least a portion of the length of the smear; quantifying a plurality of color parameters along an axis of the ROI and recording the position of each value along the axis; comparing each of the color parameters of the plurality to identify an anomalous value; and identifying an anomalous area of the smear based on the recorded position corresponding to the anomalous value.

In some aspects, the axis is in an orientation selected from the group consisting of: parallel to the direction of the smear, perpendicular to the direction of the smear and at a 45° angle with the direction of the smear.

In other aspects, the ROI spans at least a portion of the length of the examination area of the smear including e.g., at least half of the length of examination area of the smear or at least 90% of the length of the examination area of the smear.

In other aspects, the method includes separating the digital color image into individual color channels, including e.g., wherein the separating is performed after defining the ROI.

In other aspects, the plurality of color parameters comprises the mean intensity of an individual color channel. In some aspects, color coefficients are calculated for each of the plurality of color parameters and the comparing step includes comparing each of the calculated color coefficients to identify the anomalous value.

Aspects of the instant disclosure include a system for assessing a histologically stained specimen, the system comprising: a microscope; a digital color camera attached to the microscope and configured to obtain a digital color image of the specimen; a library comprising a plurality of reference color signatures specific to biological features of histologically stained reference specimens; image processing circuitry configured to: i) define on the digital color image a region of interest (ROI) based on a biological feature of the specimen; ii) separate the digital color image into individual color channels; and iii) determine a color signature for the ROI, wherein the color signature comprises quantification of one or more color parameters over the ROI for one or more of the individual color channels; and iv) compare the determined color signature to one or more reference color signatures of the plurality of reference color signatures of the library to assess the histologically stained specimen.

In some aspects, the system comprises a single memory connected to the image processing circuitry that stores the library and is configured to receive the digital color image. In other aspects, the system comprises a first memory connected to the image processing circuitry that stores the library and a second memory connected to the image processing circuitry configured to receive the digital color image.

In other aspects, the system further comprises a signal system to report the result of the assessment.

In other aspects, the one or more color parameters comprises the mean intensity of an individual color channel. In some aspects, the color signature comprises a color coefficient calculated by determining the ratio of the mean intensity value for a first color channel to the mean intensity value for a second color channel. In some aspects, the color signature comprises a first color coefficient calculated by determining the ratio of the mean intensity value for a first color channel to the mean intensity value for a second color channel and a second color coefficient calculated by determining the ratio of the mean intensity value for a third color channel to the mean intensity for the first or the second color channel. In some aspects, the color signature further comprises a third color coefficient calculated by determining the ratio of the first color coefficient to the second color coefficient.

In other aspects, the plurality of reference color signatures are derived from reference histologically stained specimens.

In other aspects, the system assesses whether the determined color signature is within a predetermined range and, when within the range, the specimen is released for further processing. In other aspects, the system assesses whether the determined color signature is outside of a predetermined range and, when outside the range, the specimen is held to prevent further processing.

In other aspects, the system assesses histological stain quality. In some aspects, the image processing circuitry is further configured to identify the ROI based on the assessment and/or to differentiate the ROI from other features of the image based on the assessment.

Aspects of the instant disclosure include a system for assessing the quality of a histologically stained specimen, the system comprising: a microscope; a digital color camera attached to the microscope and configured to obtain a digital color image of the specimen; a library comprising a plurality of reference quality color signatures specific to biological features of histologically stained reference specimens; image processing circuitry configured to: i) define on the digital color image a region of interest (ROI) based on a biological feature of the specimen; ii) determine a color signature for the ROI, wherein the color signature comprises quantification of one or more color parameters over the ROI; and iii) compare the determined color signature to one or more reference quality color signatures of the plurality of reference quality color signatures of the library to assess the quality of the histologically stained specimen.

In some aspects, the system comprises a single memory connected to the image processing circuitry that stores the library and is configured to receive the digital color image. In other aspects, the system comprises a first memory connected to the image processing circuitry that stores the library and a second memory connected to the image processing circuitry configured to receive the digital color image.

In other aspects, the system further comprises a signal system to report the result of the assessment.

In other aspects, the image processing circuitry is further configured to separate the digital color image into individual color channels. In some aspects, the one or more color parameters comprises optical density, hue, lightness, saturation and/or the mean intensity of an individual color channel.

In other aspects, the color signature comprises two or more color parameters selected from the group consisting of: optical density, hue, lightness, saturation and the mean intensity of an individual color channel. In some aspects, the color signature comprises three or more color parameters selected from the group consisting of: optical density, hue, lightness, saturation and the mean intensity of an individual color channel.

In other aspects, the color signature comprises a cytoplasmic stain color vector (CSCV). In some aspects, the CSCV is determined based on red, green and blue color channels and is calculated according to the equation: $CSCV_{rgb} = \sqrt{(Mean_{red})^2 + (Mean_{green})^2 + (Mean_{blue})^2}$, wherein "Mean" represents the mean intensity value for each color channel over a ROI comprising the cytoplasm of a cell or a portion thereof. In some aspects, the CSCV comprises one or more directional components calculated according to the equation: $\beta_{CSCV_{rgb}} = \cos^{-1}(Mean_{blue}/CSCV_{rgb})$ or the equation: $\theta_{CSCV_{rgb}} = (\cos^{-1}(Mean_{red}))\sqrt{(Mean_{red})^2 + (Mean_{green})^2}$ or a combination thereof.

In other aspects, the cytoplasmic stain color vector is determined based on hue, saturation and luminosity values and is calculated according to the equation: $CSCV_{hsl} = \sqrt{(Mean_{hue})^2 + (Mean_{saturation})^2 + (Mean_{luminosity})^2}$, wherein "Mean" represents the mean hue, saturation and luminosity values over a ROI comprising the cytoplasm of a cell or a portion thereof. In some aspects, the CSCV comprises one or more directional components calculated according to the equation: $\beta_{CSCV_{hsl}} = \cos^{-1}(Mean_{lightness}/CSCV_{hsl})$ or the equation: $\theta_{CSCV_{hsl}} = (\cos^{-1}(Mean_{hue}))\sqrt{(Mean_{hue})^2 + (Mean_{saturation})^2}$ or a combination thereof.

In other aspects, the color signature comprises a nuclear stain color vector (NSCV). In some aspects, n the nuclear stain color vector is determined based on red, green and blue color channels and is calculated according to the equation: $NSCV_{rgb} = \sqrt{(Mean_{red})^2 + (Mean_{green})^2 + (Mean_{blue})^2}$, wherein "Mean" represents the mean intensity value for each color channel over a ROI comprising the nucleus of a cell or a portion thereof. In some aspects, the NSCV comprises one or more directional components calculated according to the equation: $\beta_{NSCV_{rgb}} = \cos^{-1}(Mean_{blue}/NSCV_{rgb})$ or the equation: $\theta_{NSCV_{rgb}} = (\cos^{-1}(Mean_{red}))\sqrt{(Mean_{red})^2 + (Mean_{green})^2}$ or a combination thereof.

In other aspects, the nuclear stain color vector is determined based on hue, saturation and luminosity values and is calculated according to the equation: $NSCV_{hsl} = \sqrt{(Mean_{hue})^2 + (Mean_{saturation})^2 + (Mean_{luminosity})^2}$, wherein "Mean" represents the mean hue, saturation and luminosity values over a ROI comprising the nucleus of a cell or a portion thereof. In some aspects, the NSCV comprises one or more directional components calculated according to the equation: $\beta_{NSCV_{hsl}} = \cos^{-1}(Mean_{lightness}/NSCV_{hsl})$ or the equation: $\theta_{NSCV_{hsl}} = (\cos^{-1}(Mean_{hue}))\sqrt{(Mean_{hue})^2 + (Mean_{saturation})^2}$ or a combination thereof.

In other aspects, the color signature comprises the ratio a cytoplasmic stain color vector to a nuclear stain color vector. In some aspects, the plurality of reference quality color signatures are derived from reference histologically stained specimens of known quality.

In other aspects, the system assesses whether the determined color signature is within a predetermined range and, when within the range, the specimen is identified as adequate quality and released for further processing. In some aspects, the system assesses whether the determined color signature is outside of a predetermined range and, when outside the range, the specimen is identified as inadequate quality and held to prevent further processing.

Aspects of the instant disclosure include a non-transitory computer readable medium storing instructions that, when executed by a computing device, cause the computing device to perform the steps of: defining on a digital color image of a histologically stained specimen a region of interest (ROI) based on a biological feature of the specimen; determining a color signature for the ROI, wherein the color signature comprises quantification of one or more color parameters over the ROI; and comparing the determined color signature to a reference color signature that is specific to the biological feature and the histological stain to assess the histologically stained specimen.

Aspects of the instant disclosure include a non-transitory computer readable medium storing instructions that, when executed by a computing device, cause the computing device to perform the steps of: defining on a digital image a region of interest (ROI) spanning at least a portion of the length of the smear; quantifying a plurality of color parameters along an axis of the ROI and recording the position of each value along the axis; comparing each of the color parameters of the plurality to identify an anomalous value; and identifying an anomalous area of the smear based on the recorded position corresponding to the anomalous value.

BRIEF DESCRIPTION OF THE FIGURES

FIGS. 4A and 4B depicts the evaluation of eosinophil coloration from images of Wright-Giemsa stained smears.

DEFINITIONS

Figure 1:
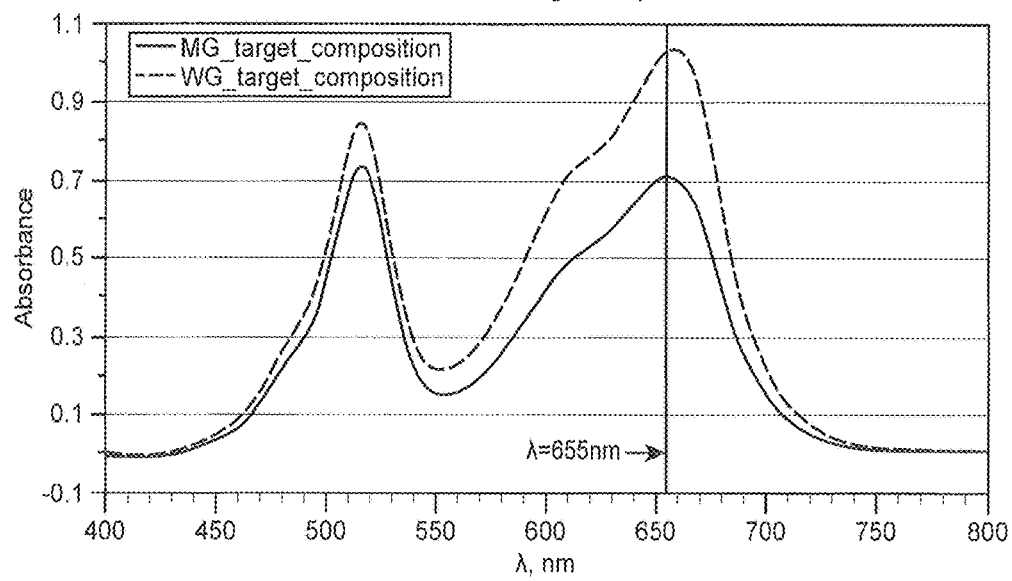
FIG. 1 depicts examples of absorption spectra for two types of Romanowsky stains.

The term "assessing" includes any form of measurement, and includes determining if an element is present or not. The terms "determining", "measuring", "evaluating", "assessing" and "assaying" are used interchangeably and include quantitative and qualitative determinations. Assessing may be relative or absolute. "Assessing the identity of" includes determining the most likely identity of a particular compound or formulation or substance or cell type or cell compartment or sub-cellular structure or cell morphology feature, and/or determining whether a predicted compound or formulation or substance or cell type or cell compartment or sub-cellular structure or cell morphology feature is present or absent. "Assessing the quality of" includes making a qualitative or quantitative assessment of quality e.g., through the comparisons of a determined value to a reference or standard of known quality.

The term "histology" and "histological" as used herein generally refers to microscopic analysis of the cellular anatomy and/or morphology of cells obtained from a multicellular organism including but not limited to plants and animals. As such, a "histological stain" refers to a stain used in the analysis of cellular anatomy and/or morphology and a "histology analyzer" refers to an instrument that analyzes the anatomy and/or morphology of cells obtained from a multicellular animal. As used herein a histology analyzer will generally refer to an instrument that uses one or more histological stains to make a histological assessment.

The term "cytology" and "cytological" as used herein generally refers to a subclass of histology that includes the microscopic analysis of individual cells, dissociated cells, loose cells, clusters of cells, etc. Cells of a cytological sample may be cells in or obtained from one or more bodily fluids. As such, a "cytological stain" refers to a stain used in the analysis of individual cells, dissociated cells, loose cells, clusters of cells, etc. and a "cytology analyzer" refers to an instrument that analyzes the anatomy and/or morphology of individual cells, dissociated cells, loose cells, clusters of cells, etc. As used herein a cytology analyzer will generally refer to an instrument that uses one or more cytological stains to make a cytological assessment.

The term "bodily fluid" as used herein generally refers to fluids derived from a "biological sample" which encompasses a variety of sample types obtained from an individual or a population of individuals and can be used in a diagnostic, monitoring or screening assay. The definition encompasses blood and other liquid samples of biological origin. The definition also includes samples that have been manipulated in any way after their procurement, such as by mixing or pooling of individual samples, treatment with reagents, solubilization, or enrichment for certain components, such as nucleated cells, non-nucleated cells, pathogens, etc.

The term "biological sample" encompasses a clinical sample, and also includes cells in culture, cell supernatants, cell lysates, serum, plasma, biological fluid, and tissue samples. The term "biological sample" includes urine, saliva, cerebrospinal fluid, interstitial fluid, ocular fluid, synovial fluid, blood fractions such as plasma and serum, and the like.

The term "inputting", as used herein, is used to refer to any way of entering information into a computer, such as, e.g., through the use of a user interface. For example, in certain cases, inputting can involve selecting a reference spectrum or a spectral characteristic or library thereof that is already present on a computer system. In other cases, inputting can involve adding a spectrum or a spectral characteristic to a computer system, e.g., by measuring the spectrum of a sample on a device capable of interfacing with a computer. Inputting can also be done using a user interface.

As used herein, the term "executing" is used to refer to an action that a user takes to initiate a program.

The terms "control", "control assay", "control sample" and the like, refer to a sample, test, or other portion of an experimental or diagnostic procedure or experimental design for which an expected result is known with high certainty, e.g., in order to indicate whether the results obtained from associated experimental samples are reliable, indicate to what degree of confidence associated experimental results indicate a true result, and/or to allow for the calibration of experimental results. For example, in some instances, a control may be a "negative control" assay such that an essential component of the assay is excluded such that an experimenter may have high certainty that the negative control assay will not produce a positive result. In some instances, a control may be "positive control" such that all components of a particular assay are characterized and known, when combined, to produce a particular result in the assay being performed such that an experimenter may have high certainty that the positive control assay will not produce a positive result. Controls may also include "blank" samples, "standard" samples (e.g., "gold standard" samples), validated samples, etc.

DETAILED DESCRIPTION

The present disclosure includes methods of assessing a histologically stained specimen based on a determined color signature of a region of interest of the specimen. Such assessments may be performed for a variety of purposes including but not limited to assessing the quality of the histological stain, as part of identifying one or more biologically relevant features of the image, as part of differentiating one feature of the image from other features of the image, identifying an anomalous area of the stained specimen, classifying cells of the specimen, etc. Also provided are systems configured for performing the disclosed methods and computer readable medium storing instructions for performing steps of the disclosed methods.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Methods

The instant disclosure includes methods of assessing a histologically stained specimen from a digital color image of the specimen using a color signature determined from the image. Aspects of the disclosure include obtaining a digital color image of the histologically stained specimen and defining a region of interest (ROI) from which one or more color parameters are extracted and used to determine a color signature.

The term "color signature", as used herein, refers to a distinctive color parameter (and its value) or combination of color parameters (with corresponding values) that is representative of a ROI. The number of color parameters that make up a color signature will vary depending on various factors including but not limited to e.g., the particular ROI from which the color parameters are derived, the type of color parameters, the type of histological stain, the type of histological specimen, etc. As such, the number of color parameters that make up a color signature may range from 1 to 10 or more, including but not limited to e.g., 1 to 10, 1 to 9, 1 to 8, 1 to 7, 1 to 6, 1 to 5, 1 to 4, 1 to 3, 2 to 10, 3 to 10, 4 to 10, 5 to 10, 6 to 10, 7 to 10, 8 to 10, 1, 2, 3, 4, 5, 6, 7, 8, 9, 10, 10 or more, etc. Any individual color parameter or combination of color parameters may find use in a color signature provided the resultant color signature is representative of the ROI and sufficient to allow for an assessment as described herein.

In one embodiment, one or more color parameters of a color signature may be based on complementary colors. The term "complementary colors", as used herein, generally refers to colors directly opposite each other in the color spectrum that when combined in the right proportions, produce white light or a grayscale value. For example, absorption of 420-430 nm light renders a substance yellow, and absorption of 500-520 nm light renders a substance red. Green is unique in that it can be created by absorption near 400 nm as well as absorption near 800 nm.

Violet light, generally ranging from about 400 nm to 430 nm, is complementary to yellow light. Blue light, generally ranging from about 430 nm to 480 nm, is complementary to orange light. Green light, generally ranging from about 480 nm to 560 nm, is complementary to Red light. Yellow light, generally ranging from about 560 nm to 590 nm, is complementary to violet light. Orange light, generally ranging from about 590 nm to 630 nm, is complementary to blue light. Red light, generally ranging from about 630 nm to 750 nm, is complementary to green light. As will be readily understood, due to the spectral nature of color, the wavelength boundaries between different colors vary and thus, in some instances, the wavelengths defining a particular color may vary from those described above.

Color complements are based on the absorbance of light at one or more particular wavelengths. For example, when white light passes through a substance that absorbs light at wavelength X the transmitted light is depleted in the color of wavelength X such that the color complementary to wavelength X is dominant and the transmitted light takes on the hue of the wavelength of the color complementary to wavelength X.

Dye components of histological stains absorb light at one or more particular wavelength ranges (i.e., absorbance bands) resulting in the color of the dye. The absorbance spectra of histological stain formulations are more complex than the simple sum of the absorbances of the dye components because each component, including the dye and non-dye components, of the formulation interacts to influence the absorbance of the other dye(s) of the formulation. In addition, when applied to a specimen, the components of a histological stain formulation further interact with components of the specimen, including e.g., cellular components, where such interactions may be specific for particular cell components (e.g., cytoplasm, nucleus, etc.). The absorbances resulting from these interactions, as collected as colors in a digital color image, may be used as aspects of a color signature.

In some instances, a color signature may be derived for a particular stain or group of stains where the color parameter(s) of the signature are based on color complementarity of the dyes of the particular stain or group of stains. For example, in some instances, a color signature derived for Romanowsky stains is based on the color complementarity of Romanowsky stain dyes, including but not limited to e.g., eosin and azure/methylene blue.

In some instances, a color signature for a Romanowsky stain may include but is not limited to e.g., a red hue color parameter (e.g., a red coefficient value), a blue hue color parameter (e.g., a blue coefficient value), a blue-red balance value (e.g., a blue coefficient value divided by a red coefficient value), and combinations thereof.

In other instances, a color signature for a histologically stained specimen may include but is not limited to one or more hue color parameters including but not limited to e.g., a purple hue color parameter, a lavender hue color parameter, a deep purple hue color parameter, a light blue hue color parameter, a greyish-blue hue color parameter, a turquoise hue color parameter, a green hue color parameter, a yellow hue color parameter, a deep red hue color parameter, a raspberry hue color parameter, a pink hue color parameter, and combinations thereof.

In some instances, a color signature for a histologically stained specimen may include one or more mean color intensity color parameters including but not limited to e.g., mean values for red, mean values for green, mean values for blue, and combinations thereof.

In some instances, a color signature for a histologically stained specimen may include one or more features of a color and/or color channel of a digital image including optical density, hue, lightness, saturation, etc., including but not limited to e.g. one or more features of red and/or the red channel of a digital image (e.g., including red optical density, red hue, red lightness, red saturation, etc.), one or more features of green and/or the green channel of a digital image (e.g., including green optical density, green hue, green lightness, green saturation, etc.), one or more features of blue and/or the blue channel of a digital image (e.g., including blue optical density, blue hue, blue lightness, blue saturation, etc.).

In some instances, a color signature for a histologically stained specimen may include one or more color parameter ratios. For example, in some instances, a color signature may include the ratio of two mean intensities of two different color channels including but not limited to e.g., the ratio of the red channel intensity to the blue channel intensity, the ratio of the blue channel intensity to the green channel intensity, the ratio of the red channel intensity to the blue channel intensity, etc.

In some instances, a color signature for a histologically stained specimen may include one or more color parameter vectors that characterize the colors of a particular ROI. For example, in some instances, a color signature includes one or more nuclear stain color vectors, one or more cytoplasmic stain color vectors, etc.

As described above, various color parameters may find use in a color signature useful in making an assessment of a histologically stained specimen including but not limited to e.g., those color parameters described herein.

Color Parameters

The instant methods include quantifying one or more color parameters for use in determining a color signature that may be used in making an assessment of a histologically stained specimen. Any appropriate color parameter that may be derived from a digital color image may find use in the subject methods provided the color parameter can be used as, or as part of, a color signature sufficient to perform the assessments as described herein. As such, the actual color parameters, e.g., as make up color signature, will vary.

In some instances, a color parameter may be quantified from a color channel of the digital image. For example, in some instances, a digital color image may be split into its component channels and a color parameter may be quantified for one or more of the individual color channels, including but not limited to e.g., two or more of the individual color channels, three or more of the individual color channels, etc. Any convenient and appropriate statistical measure of the individual color channel may find use in deriving a color parameter, including but not limited to e.g., mean intensity, median intensity, etc. where the statistical measure may be calculated over the entire intensity histogram of the channel or a portion thereof including but not limited to e.g., the dynamic range portion.

In some instances, a color parameter may be quantified from a color feature or characteristic of the digital image. For example, in some instances, a color parameter may be optical density, hue, lightness, saturation, and the like. In addition, a color parameter may include where the color parameter is calculated from two or more color features including but not limited to e.g., two or more of the optical density, hue, lightness, saturation, etc., three or more of the optical density, hue, lightness, saturation, etc., four or more of the optical density, hue, lightness, saturation, etc. Any convenient and appropriate statistical measure of the color feature(s) may find use in deriving a color parameter, including but not limited to e.g., mean, median, etc. where the statistical measure may be calculated over the entire intensity histogram or a portion thereof including but not limited to e.g., the dynamic range portion.

In some instances, a color parameter may be quantified from two or more quantified color parameters. For example, in some instances, a color parameter may be quantified from two statistical measures (e.g., mean, median, etc.) of two different color channels including but not limited to e.g., quantified from statistical measures of the red and green channels, quantified from statistical measures of the red and blue channels, quantified from two statistical measures of the blue and green channels, etc.

In some instances, a color parameter that may be quantified from two or more quantified color parameters includes a color coefficient, where the color coefficient is calculated from the ratio of the mean intensity of a first channel to the mean intensity of a second channel. For example, in some instances, a red coefficient is calculated, where the red coefficient is the quotient of the mean intensity of the red channel and the mean intensity of the green channel. In some instances, a blue coefficient is calculated, where the blue coefficient is the quotient of the mean intensity of the blue channel and the mean intensity of the red channel.

In some instances, a color parameter that may be quantified from two or more quantified color parameters includes a color ratio, where a color ratio may be a simple color ratio (e.g., the ratio of the intensities of the red channel to the intensities of the green channel, etc.) or a secondary color ratio (e.g., where a ratio is derived from the ratio of two calculated simple ratios). For example, in some instances, a color parameter may be a color balance, where the color balance is calculated from the quotient of a first color coefficient and a second color coefficient. In some instances, a color parameter may be the calculated blue-red balance, where the blue-red balance is calculated from the quotient of the blue coefficient and the red coefficient.

In some instances, a color parameter that may be quantified from individual color channel statistics includes but is not limited to an ROI color vector, where an ROI color vector is calculated as the square root of the sum of all the squares of the mean channel intensities of each channel. The ROI of a ROI color vector can be any useful and appropriate ROI including but not limited to e.g., an ROI defined by a biological feature of one or more cells of the specimen including but not limited to e.g., a cell, a nucleus, a cytoplasm, etc. In some instances, an ROI color vector is a nuclear stain color vector (NSCV) or a cytoplasm stain color vector (CSCV). In some instances, a color parameter may include the ratio of two ROI color vectors.

In some instances, a CSCV can be determined based on red, green and blue color channels and is calculated according to the equation: $CSCV_{rgb} = \sqrt{(Mean_{red})^2 + (Mean_{green})^2 + (Mean_{blue})^2}$, wherein "Mean" represents the mean intensity value for each color channel over a ROI comprising the cytoplasm of a cell or a portion thereof.

In some instances, a CSCV can be determined based on hue, saturation and luminosity values and is calculated according to the equation: $CSCV_{hsl} = \sqrt{(Mean_{hue})^2 + (Mean_{saturation})^2 + (Mean_{luminosity})^2}$, wherein "Mean" represents the mean hue, saturation and luminosity values over a ROI comprising the cytoplasm of a cell or a portion thereof.

In some instances, a NSCV can be determined based on red, green and blue color channels and is calculated according to the equation: $NSCV_{rgb} = \sqrt{(Mean_{red})^2 + (Mean_{green})^2 + (Mean_{blue})^2}$, wherein "Mean" represents the mean color intensity value for each color channel over a ROI comprising the nucleus of a cell or a portion thereof.

In some instances, a NSCV can be determined based on hue, saturation and luminosity values and is calculated according to the equation: $NSCV_{hsl} = \sqrt{(Mean_{hue})^2 + (Mean_{saturation})^2 + (Mean_{luminosity})^2}$, wherein "Mean" represents the mean hue, saturation and luminosity values over a ROI comprising the nucleus of a cell or a portion thereof.

Any combination of quantified color parameters and or higher order color parameters calculated from other color parameters may find use in deriving a color signature as described herein. Combinations of color parameters will vary depending on various factors including but not limited to the histological stain used, the specimen, the purpose of the assessment and the ROI of the image.

Region(s) of Interest (ROI)

The instant methods include the derivation of color parameters from digital images where the derived color parameters may pertain to one or more regions of interest (ROI) of the image of the specimen. ROIs of the image may be any collection or pixels useful for deriving a color parameters for use in the methods as described herein. A single ROI or multiple ROIs may be defined for a particular image and, e.g., a ROI may include the entire image or essentially the entire image of the specimen or a portion thereof, e.g., as defined by some biological feature of the image (e.g., the cells of the image).

Useful ROIs for calculating color parameters include but are not limited to cellular ROIs that include one or more cells or one or more portions of a cell of the digital image. Accordingly, derived color parameters may pertain to a cell as a whole or various cellular portions including but not limited to cellular portions defined by a structural unit of a cell or cellular portions defined by some other criteria including non-structural criteria.

Structural units of a cell for which a color parameter may be derived or may be used to define a cellular portion of the cell include any subcellular component of the cell resolvable through microscopy, including those resolvable with the assistance of histological staining, including but not limited to the nucleus of the cell, the nuclear membrane of the cell, the nucleolus of the cell, the cytoplasm of the cell, the chromatin of the cell, the heterochromatin of the cell, the euchromatin of the cell, the plasma membrane of the cell, cilia of a cell, granules of the cell, mitochondria of the cell, golgi of the cell, endoplasmic reticulum of the cell, microtubules of the cell, intermediate filaments of the cell, and the like.

Non-structural criteria, as referred to herein, refers to criteria used to define a cellular portion that is not based on an underlying structural component of the cell and/or does not correlate with an underlying structural component of the cell. For example, in some instances, a non-structural criterion may be based or derived from one or more calculated positions or measures of the cell including but not limited to e.g., the center of the cell (e.g., the centroid of the cell), the perimeter of the cell, etc. In some instances, the non-structural criterion may be the calculated position or measure of the cell. In other instances, the non-structural criterion may be based on the calculated position or measure of the cell including e.g., one or more circles within the cell (e.g., as calculated from the centroid of the cell), one or more annuli within the cell (e.g., as calculated from the centroid of the cell), one or more semicircles within the cell (e.g., as calculated from the centroid of the cell), one or more sectors of the cell (e.g., circular sectors, or approximation thereof, as calculated from the centroid of the cell), one or more segments of the cell (e.g., circular segments, or approximation thereof, as calculated from the centroid of the cell), and the like.

As will be readily understood, structural units and non-structural units of a cell, including combinations of different structural units, different non-structural units and structural unit and non-structural unit combinations, that may be used to define a cellular portion may, in some instances, also be used to define a ROI as described herein.

In some instances, a portion of a subcellular component (e.g., a portion of the cytoplasm, a portion of the nucleus, a portion of the cell, etc.) may be used to define a ROI as described herein including, e.g., where the portion of the subcellular component is some percentage of a cellular structure including but not limited to e.g., 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, 100%, etc., of the subcellular component.

In some instances, color parameters may be determined over one or more cellular ROI that includes the entirety of a cell or essentially the entire cell. In some instances, color parameters may be determined over one or more ROIs of a cellular portion (including cell structure defined and non-structurally defined portions) or an ROI that includes one or more cellular portions (e.g., the cytoplasm of the cell, the nucleus of the cell, etc.).

In some instances, color parameters may be determined over one or more non-cellular portions of a digital image (including but not limited to e.g., the background of the image or portion thereof).

Digital Color Images

Digital color images of the subject methods may be newly acquired, e.g., including where the image is processed immediately following acquisition or may have been previously acquired and e.g., may be stored for some length of time on a suitable device or medium prior to processing. In some instances, previously acquired images may be stored in a database including e.g., a database of pre-collected images for later analysis, a database of pre-collected images pertaining to a particular patient, a database of pre-collected images pertaining to a particular histological analysis device, a database of pre-collected images pertaining to a particular stain or stain manufacturer, a database of pre-collected images pre-collected images pertaining to a particular histological analysis laboratory, etc.

In some instances, a pre-collected image may be stored and analyzed according to the instant disclosure only after primary histological analysis is performed on the image. By "primary histological analysis" is meant the histological analysis performed on the specimen for one more medical purposes including but not limited to e.g., screening, diagnosis, prognosis, etc. Analysis of pre-collected images for which primary histological analysis of the specimen has already been performed may be performed for a variety of reasons including for example, assessing or confirming the quality of the histological stain used on the specimen.

Acquired digital color images may be captured using any suitable color enabled image capturing device. Suitable digital color image capturing devices will be stand-alone image capture units or may be an integrated image capturing device that is part of a larger analysis system including e.g., a histology analyzer, an automated microscopy system, a hematology analyzer, a cytology analyzer, an imaging flow cytometer, an imaging microfluidics system, etc. Suitable digital color image capturing devices will vary greatly depending on the particular imaging context, the purposes of image capture and the associated components of the device or system as a whole.

At a minimum a suitable color image capturing device, for use in the described methods, will include a digital color camera capable of capturing a digital color image and a means of storing the digital color image and/or transferring the image to attached image processing circuitry or to an attached storage device for later transfer to image processing circuitry. Suitable digital color cameras will vary and will generally include any digital color camera with sufficiently high resolution and sufficient color capture to capture an image that may be processed according to the methods described herein.

Aspects of the disclosed methods include obtaining a digital color image of histologically stained cells by capturing a digital color image of a histologically stained specimen from a subject where the specimen contains histologically stain cells or is prepared to include histologically stain cells. In some instances, the histologically stained cells include hematologically stained cells.

In other instances, obtaining a digital color image of histologically stained cells may include receiving a digital color image including e.g., where the digital color image is received from various sources including but not limited to an integrated imaging device, an external imaging device, a computer memory, a computer readable medium, a server, a remote server, etc. Digital color images may be received by a data or computer connection or may be received on a computer readable medium.

A "digital image", as used herein, generally refers to a numeric representation (e.g., binary representation) of a two-dimensional image that may be of fixed or unfixed resolution. Fixed resolution images have a fixed number of rows and columns of pixels in an XY orientation. In some instances, digital images may be three-dimensional having fixed number of voxels in a XYZ orientation. Pixels and voxels are stored in computer memory as a raster image or raster map, a two-dimensional or three-dimensional array of small integers transmitted or stored in an uncompressed or compressed form. Suitable digital image file formats include but are not limited to e.g., BMP, BPG, CD5, DEEP, ECW, Exif, FITS, FLIF, GIF, HDR, HEIF, ILBM, ILBM, IMG, IMG, JPEG 2000, JPEG XR, JPEG/JFIF, Layered Image File Format, Nrrd, PAM, PBM, PCX, PGF, PGM, PLBM, PNG, PNM, PPM, SGI, SID, Sun Raster, TGA, TIFF, VICAR, WEBP, and the like.

Digital images may be a variety of image bit depths depending, e.g., on the particular type of image captured (e.g., color or grayscale) and the sensitivity of the digital camera or other image capture device and may include but are not limited to e.g., 8-bit, 10-bit, 12-bit, 14-bit, 16-bit, 18-bit, 24-bit, 30-bit, 36-bit, 48-bit, 64-bit, and the like. In some instances, the channels of a color image may individually be or may be split into individual 8-bit grayscale images. In some instances, the channels of a color image may individually be or may be split into individual 16-bit grayscale images. In some instances, a digital color image may be generated from multiple individually captured grayscale images that are combined into a single image by assigning the individually captured grayscale images to different color channels of the single image. In other instances, all the colors of a digital color image are captures simultaneously, e.g., through the use of an image capture device having multiple photo detectors assigned to different colors and one or more optical devices for directing light of different colors to different photo detectors.

Digital images may be binary (e.g., black and white), grayscale or color formats and may be converted between formats by suitable image processing algorithms. For example, a color image may be "split" into individual color channels to produce individual grayscale images for each color channel. For example, a red, green and blue image (RGB) image may be split into individual red, green and blue channels to produce a grayscale image of the red channel, a grayscale image of the green channel and a grayscale image of the blue channel. Color images may be converted between color spaces and split into any convenient and appropriate color channels of a particular color space including but not limited to e.g., RGB color space, CMYK color space, HSV color space, CIE color space, Lab color space, CIELUV color space, YCbCr color space, and the like. Binary images and grayscale images may be applied to a channel of a color image and, e.g., where multiple binary or grayscale images are applied to multiple channels of a color image, a color image may be constructed, or "merged", from binary and/or grayscale images. Where a color image is split into individual color channels to produce grayscale images, an individual grayscale image may be referred to by its prior channel designation, e.g., a grayscale image produced from the red channel may be referred to as "red" in subsequent steps and/or any values generated from the "red" channel may be referred to by their prior channel designation, e.g., the mean "red" intensities refers to the mean intensity values derived from the grayscale image produced from the red channel. Images and values derived from other color spaces may be referred to using corresponding nomenclature.

Accordingly, digital color images may be processed as color images (i.e., as multichannel images) or may be converted or split into two or more individual color channels prior to processing. When split into two or more individual color channels prior to processing, any number of the resulting split images may be used in further processing steps including but not limited to all the split images (i.e., all the individual channels of the image) or only one of the split images (i.e., only one of the individual channels of the image) or one or more, including but not limited to two or more, three or more, two, three, etc. of the split images (i.e., the individual channels of the image).

Digital color images may be segmented prior to processing for one or more color parameters. As used herein, the terms "segmented" and "segmentation" as they relate to image processing generally refer to the division or partitioning of an image into meaningful structures or segments. Various methods for image segmentation may find use in the methods described herein or in preparation of an image for processing according to the methods as described herein. Selection of a particular segmentation method or combination of segmentation methods will depend on various factors including the type of image captured, the nature of subject matter of the image, the desired result of the image processing, the one or more color parameters determined, etc.

In some instances, image segmentation may make use of one or more of threshold based segmentation, edge based segmentation and region based segmentation. Specific image segmentation methods include but are not limited to thresholding methods, clustering methods, compression-based methods, histogram-based methods, edge detection methods, dual clustering methods, region-growing methods, partial differential equation-based methods (e.g., parametric methods, level set methods, fast marching methods, etc.), variational methods, graph partitioning methods (e.g., Markov Random Fields methods), watershed transformation methods, model based segmentation methods, multi-scale segmentation methods, semi-automatic segmentation methods, trainable segmentation methods, and the like.

Other digital image processing image transformations that may find use in the described methods include but are not limited to e.g., point processing transformations (e.g., negative transform, log transform, inverse log transform, nth root transform, nth power transform, gamma correction, contrast transforms (e.g., contrast stretching), window center correction, histogram equalization, etc.), filtering (i.e., neighbor) transformations (e.g., mean filters, Gaussian filters, median filters, image gradient filters, Laplacian filters, normalized cross correlation (NCC) filters, etc.), and the like.

Following image processing (e.g., image segmentation, image transformation, etc.) an image mask may be generated. As used herein the terms "mask", as related to image processing, and "image mask" collectively refer to spatial filtering of a digital image so as to limit further processing steps to a defined subset or defined portion of the original image. For example, in some instances, a digital image may be segmented to partition one or more regions of interest (ROI) and an image mask may be generated based on the segmented ROI such that further image processing steps are limited only to those pixels contained within the mask defined by the segmented ROI. Various masks may be generated depending on the particular processes to be performed. In some instances, an image mask may involve discarding the image information not contained within the mask. In some instances, a new image is produced from an image mask containing only the information contained within the mask.

In some instances, a digital image may be segmented according to cellular boundaries and the cellular boundaries may be the basis for defining an ROI where the ROI comprises one or more cells defined by the segmentation. In some instances, an ROI may comprise all of the segmented cells of the image or a subset of the segmented cells of the image, e.g., based on some criteria including but not limited to e.g., size, shape, brightness, color, etc. In some instances an ROI based on or comprising segmented cells may serve as the basis for generating a cellular mask that contains all or a portion of the segmented cells. A cellular mask may limit a further image processing step to only those pixels contained within the cellular mask and/or only those cellular structures contained within the cellular mask.

In some instances, a digital image may be segmented according to nuclear boundaries and the nuclear boundaries may be the basis for defining an ROI where the ROI comprises one or more nuclei defined by the segmentation. In some instances, an ROI may comprise all of the segmented nuclei of the image or a subset of the segmented nuclei of the image, e.g., based on some criteria including but not limited to e.g., size, shape, brightness, color, etc. In some instances an ROI based on or comprising segmented nuclei may serve as the basis for generating a nuclear mask that contains all or a portion of the segmented nuclei. A nuclear mask may limit a further image processing step to only those pixels contained within the nuclear mask and/or only those nuclear structures contained within the nuclear mask. In some instances, a digital image may be segmented according to or an ROI may be generated based on a subsection of the nucleus of a cell, including but not limited to e.g., one or more nuclear lobes of the nucleus of the cell.

In some instances, a digital image may be segmented according to cytoplasm boundaries and the cytoplasm boundaries may be the basis for defining an ROI where the ROI comprises one or more cellular cytoplasms defined by the segmentation. In some instances, an ROI may comprise all of the segmented cytoplasms of the image or a subset of the segmented cytoplasms of the image, e.g., based on some criteria including but not limited to e.g., size, shape, brightness, color, etc. In some instances an ROI based on or comprising segmented cytoplasms may serve as the basis for generating a cytoplasmic mask that contains all or a portion of the segmented cytoplasms. A cytoplasm mask may limit further image processing step to only those pixels contained within the cytoplasm mask and/or only those cellular structures contained within the cytoplasm mask.

Any useful ROI and/or mask may be generated according to any cellular structure or cellular substructure discernable on the digital color image. In some instances, multiple cellular ROIs and/or masks may be combined in an image processing step, e.g., such that further image processing steps are confined to those pixels defined by some combination of ROIs and/or masks including but not limited to e.g., a combination of cellular and nuclear ROIs and/or masks, a combination of nuclear and cytoplasmic ROIs and/or masks, a combination of cellular and cytoplasmic ROIs and/or masks, etc.

In some instances, two or more different ROIs and/or masks may be compared such that image processing steps are performed on each of the two or more different ROIs and/or masks and the ROIs and/or masks themselves or resultant values therefrom are compared. For example, in some instances a cellular ROIs and/or mask may be compared to a nuclear ROIs and/or mask, a nuclear ROIs and/or mask may be compared to a cytoplasmic ROIs and/or mask, a cellular ROIs and/or mask may be compared to cytoplasmic ROIs and/or mask, etc.

It will be understood that ROIs and/or masks are not limited to cellular structures and a mask may be defined for any spatial or non-spatial component of the digital image. For example, in some instances a background ROIs and/or mask may be generated including but not limited to e.g., a slide-background ROI and/or mask, which includes all or a portion of the background of the digital image, i.e., the non-cellular portions of the slide captured in the digital image. Non-spatial masks that may be employed include but are not limited to e.g., noise masks, threshold masks, etc.

Following pre-processing of the digital image (e.g., image segmentation, image transformation, etc.) one or more color parameters may be derived from the digital color image and such color parameters may be derived over a defined region of the digital color image, e.g., defined by a ROI, defined by a mask, etc. In some instances, one or more color parameters may be derived from the digital color image, including where the color parameter is derived over a defined region of the digital color image, without prior pre-processing of the digital image.

Assessments

The instant methods include one or more assessments of a histologically stained specimen based on a color signature determined from a digital color image of the histologically stained specimen. Such assessments will vary depending, e.g., on the type of specimen, the histological stain used, the ROI assessed, etc. Assessments made according to the described methods include but are not limited to e.g., assessments of histological stain quality, assessments of ROI coloration, and the like.

In some instances, the methods of the instant disclosure include quality assessments of a histologically stained specimen and/or quality assessments of a histological stain. According to the instant disclosure histological stain quality assessments described include where the histological stain is assessed following staining of the specimen. Such post-staining assessments are valuable in that the stain is assessed in its final form where no preparation and/or staining steps remain, thus the stain assessment is reflective of the final stain and its performance in the final application of the stain.

In some instances, stain quality may be assessed to determine whether the histological stain and/or histological stained specimen is adequate for the intended purpose. By "adequate" is meant that the stained specimen is sufficient to make a conclusion according to the intended purpose of the histologically stained specimen. Conclusions made from adequately stained specimens will vary and may include e.g., a cell identification conclusion where the stain is adequate for a human observer to identify a cell type of a histologically stained specimen, a cell identification conclusion where the stain is adequate for an automated cell analysis system to properly identify a cell type of a histologically stained specimen, a diagnostic conclusion where the stain is adequate for a diagnosis to be made, etc.

In some instances, stain quality is assessed prior to primary histological analysis and a determination of whether the quality of the stain is adequate is made prior to further histological analysis. For example, in some instances, only after a histological specimen is determined to be adequate is primary histological analysis performed. In other instances, stain quality is assessed after primary histological analysis and a determination of whether the quality of the stain was adequate is made after the histological analysis. For example, in some instances, after primary histological analysis is performed the digital image may be assessed to determine the quality of the histological stain to, e.g., provide a determination as to the reliability of the primary histological analysis. In yet other instances, stain quality is assessed concurrently with primary histological analysis.

Quality assessments of the instant disclosure include evaluating histological stains and histologically stained specimens used in a variety of applications including but not limited to e.g., clinical applications, preclinical applications, research applications, veterinary applications, instrument testing applications, etc. As such, the stringency of the quality assessment may vary e.g., depending on the particular application in which the stain is employed. As such, the adequacy of the stain may be assessed relative to the intended application of the stain where, e.g., clinical applications (including e.g., diagnostic, prognostics, etc.) may require higher quality for stain adequacy as compared to other applications.

A quality assessment, as described herein, will generally involve a comparison of a determined color signature with a reference color signature where the comparison reveals whether the histological stain or histologically stained specimen is adequate or inadequate for the intended purpose.

In some instances, the methods of the instant disclosure include assessments of ROI coloration. ROI coloration assessments generally involve determining the coloration based on a color signature of an ROI of the specimen, where such assessments may be performed for a variety of purposes and ROIs useful in such assessments also vary. For example, in some instances, a ROI coloration assessment may include an ROI defined by a cell and the coloration of the cell may be performed as part of an analysis to determine whether the cell is normal or abnormal. In some instances, a ROI coloration assessment may include an ROI defined by a nucleus and the coloration of the nucleus may be performed as part of an analysis to determine whether the nucleus and/or the cell containing the nucleus is normal or abnormal.

In some instances, ROI coloration assessments include where the assessment is used as part of a process of cell classification. For example, in some instances, coloration assessments are performed for a plurality of ROIs defined by cells of the specimen and the cells are categorized according to their respective coloration assessments. Accordingly, ROI coloration assessments may find use in automated cell classification determinations including but not limited to e.g., those included in automated hematology assessments, e.g., automated hematology screening, automated hematology cell counting, etc.

A ROI coloration assessment, as described herein, will generally involve a comparison of a determined color signature with a reference color signature where the comparison reveals whether the histological stain or histologically stained specimen is adequate or inadequate for the intended purpose.

Reference values for a color signature (i.e., a reference color signature) will vary depending on the particular histological stain, the particular specimen, the assessment performed, etc. and may include but are not limited to e.g., target values, ranges, thresholds, etc. For example, in some instance a reference value may be a target value or may include a plurality of target values such that a determined color signature is compared to the target value or plurality of target values to determine if a match is found, e.g., if the measured color signature matches one or more of the target values. In some instances, when the comparison reveals a match, the subject histological stain is determined to be adequate. In other instances, when the comparison fails to reveal a match the subject histological stain is determined to be inadequate.

In some instance a reference color signature may be a target range or may include a plurality of target ranges such that a determined color signature is compared to the target range or plurality of target ranges to determine if the value of the determined color signature is within the range. In some instances, when the comparison reveals that the determined color signature is within the range the subject histological stain is determined to be adequate. In other instances, when the comparison reveals that the determined color signature is within the range the subject histological stain is determined to be inadequate. In yet other instances, when the comparison reveals that the determined color signature is outside the range the subject histological stain is determined to be adequate. In yet other instances, when the comparison reveals that the determined color signature is outside the range the subject histological stain is determined to be inadequate. Accordingly, a target range may be a target range for stain adequacy or a target range for stain inadequacy.

In some instances a reference color signature may be a threshold or may include a plurality of thresholds such that a determined color signature is compared to the threshold or plurality of thresholds to determine if the determined color signature is above or below the threshold. In some instances, when the comparison reveals that the determined color signature is above the threshold the subject histological stain is determined to be adequate. In other instances, when the comparison reveals that the determined color signature is above the threshold the subject histological stain is determined to be inadequate. In yet other instances, when the comparison reveals that the determined color signature is below the threshold the subject histological stain is determined to be inadequate. In yet other instances, when the comparison reveals that the determined color signature is below the threshold the subject histological stain is determined to be adequate. Accordingly, a threshold may be a threshold for assessing adequacy of a histological stain or a threshold for assessing adequacy of a histological stain based on whether the corresponding determination requires that the value is above or below the threshold.

Values for reference color signatures including e.g., target values, ranges, thresholds, etc., may be determined by a variety of methods. For example, in some instances, reference color signatures may be generated by calculating the color signature for a known sample, e.g., a control sample, a known adequately stained histological sample, a known inadequately stained histological sample, a stained histological sample that has been verified by some other means (including e.g., verified to be adequate for histology analysis by an expert, verified to be inadequate for histology analysis by an expert, verified to be a "gold standard" histologically stained sample, etc.), etc.

Reference color signatures may be predetermined, e.g., determined or calculated prior to performing an assessment as described herein. In some instances, a predetermined reference color signature may be determined from a control sample prior to the assessment. In other instances, a predetermined reference color signature may be determined and may be stored, e.g., stored electronically on a computer readable medium or a computer memory, for use in an assessment as described herein, e.g., as in a library of reference color signatures.

Specimens

The instant methods include determining a color signature from a digital color image of a histologically stained specimen. Histologically stained specimens include those biological samples and/or bodily fluids prepared with histological stains for analysis of cell morphology. In some instances, histologically stained specimens include but are not limited to hematological samples prepared from blood and containing blood cell types including but not limited to nucleated blood cells, enucleated blood cells, white blood cells, nucleated red blood cells, red blood cells, giant platelets, leukocytes, basophils, eosinophils, lymphocytes, monocytes, neutrophils, platelets, bone marrow cells, etc.

In some instances, methods described herein may include preparing a histologically stained specimen from a subject where the specimen contains histologically stain cells or is prepared to include histologically stain cells. In other instances, the specimen may be previously prepared and the method may include processing a digital color image obtained from a histologically stained specimen from a subject. By "preparing", in this context, is meant all or some of the steps of applying a biological sample, including a bodily fluid sample, onto a substrate (e.g., a slide, plate, coverslip, etc.) or into a vessel (e.g., a well, a dish, a flask, etc.) and configuring the sample for analysis through physical and/or chemical manipulation (including e.g., spreading, mounting, mixing, staining, counter-staining, bleaching, etc.). A biological sample may be prepared directly after being obtained from the subject or may be stored for some time in an appropriate storage container (including e.g., a specimen bag, a specimen tube, a specimen dish, etc.) prior to being prepared for histological analysis.

As used herein, histology stains refer to those stains used in microscopic analysis of the cellular anatomy and/or morphology of cells obtained from a multicellular organism. Histology stains generally include at least one dye that stains one or more cell types and/or components of one or more cell types a contrasting color. Histology stains may also include at least one counter-stain that stains the rest of the cells or the rest of the cell a different color. Histological techniques, stains and staining methods are well-known and include but are not limited to those described in Kiernan. Histological and histochemical methods: Theory and practice. Oxford: Butterworth/Heinemann, 1999 and Bancroft & Stevens. Theory and practice of histological techniques. New York, N.Y.: Churchill Livingstone, 1996; the disclosures of which are incorporated herein by reference in their entirety.

Histological staining techniques can be specific, staining one or more particular cells in a specific way, or non-specific, staining essentially all cells or most cells in the same or similar way. Histology stains include but are not limited to e.g., Alcian blue stains, Aniline blue stains, Azan stains, Biebrich scarlet-acid fuchsin stains, Carbol-fuchsin stains, Chrome alum/haemotoxylin stains, Congo Red stains, Crystal violet stains, Fast Red stains, Hematoxylin and Eosin (H&E) stains, Iron Hematoxylin stains, Isamin blue/eosin stains, Jenner's stains, Mallory's Phosphotungstic Acid Hematoxylin (PTAH) stains, Mallory's Trichrome stains, Masson stains, Malachite Green stains, Methyl Green-Pyronin (MGP) stains, Nissl and methylene blue stains, Nissl stains, Oil Red O stains, Orcein stains, Osmic Acid stains, Osmium Tetroxide stains, Papanicolaou stains, Periodic Acid-Schiff (PAS) stains, Reticulin stains, Romanowsky stains, Safranin O stains, Silver stains, Sudan Black and osmium stains, Toluidine-blue stains, Trichrome AB, Trichrome LG, Trypan Blue stains, van Gieson stains, Verhoff's stains, Weigert's resorcin-fuchsin stains, and the like.

Dyes included in histology stains will vary depending on the stain formulation and the desired staining result. In some instances, dyes useful in histology stains may include but are not limited to, e.g., Acid Fuchsin calcium salt, Acid fuschin, Alcian Blue, Alizarin Red, Aniline blue, Aniline Blue diammonium salt, Auramine O Dye, Azure, Azure A chloride, Azure B, Basic Fuchsin, Bismarck Brown Y, Brilliant Cresyl Blue, Brilliant Green, Carmine, Congo Red, Cresyl Violet acetate, Crystal Violet, Darrow Red, Eosin, Eosin B, Eosin Y, Eosin Y disodium salt, Erythrosin B, Erythrosin extra bluish, Ethyl eosin, Fast Green FCF, Hematoxylin, Indigo carmine, Janus Green B, Light Green SF Yellowish, Malachite Green oxalate salt, Methyl Blue, Methyl green, Methyl Green zinc chloride, Methyl Orange, Methyl violet 2B, Methylene blue, Methylene Violet (Bernthsen), Neutral Red, Nigrosin, Nile Blue A, Oil Red O, Orange G, Orange II sodium salt, Orcein synthetic, Phloxine B Dye, Pyronin B, pyronin G, Pyronin Y, Resazurin sodium salt, Rose Bengal sodium salt, Safranin O, Sudan Black B, Sudan III, Sudan IV, Thionin acetate salt, toluidine, Toluidine Blue O, and the like.

Histological stains include Romanowsky stains. Romanowsky stains are generally neutral stains composed of various components including but not limited to methylene blue (e.g., Azure B) and eosin (e.g., Eosin Y) dyes. Azures are basic dyes that bind acid nuclei and result in a blue to purple color. Eosin is an acid dye that is attracted to the alkaline cytoplasm producing red coloration. Romanowsky stains vary and include various formulations including those containing various azure and eosin analogs. Romanowsky stains and their mechanisms of staining are well-known and described in e.g., Horobin & Walter. Histochemistry (1987) 86:331-336; Marshall et al. J Clin Pathol (1978) 31(3):280-2; Marshall et al. J Clin Pathol. (1975) 28(11):920-3; J Clin Pathol (1975) 28(8):680-5; the disclosures of which are incorporated herein by reference.

Romanowsky stains include but are not limited to Giemsa Stain, Wright Stain, Wright Giemsa Stain, Jenner Stain, Jenner-Giemsa Stain, Leishman Stain, May Grunwald Stain, May Grunwals Giemsa Stain, and the like. Each Romanowsky stain may exist in various formulations either as derived from various different recipes or as supplied from various providers. Romanowsky stain formulations may include various stain components including but not limited to e.g., methylene blue, azure A, azure B, azure C, toluidine blue, thionine, methylene violet Bernthsen, methyl thionoline, thionoline, eosin, eosin Y, tribromofluorescein, fluorescein, thiazine dyes, and the like. Romanowsky stain formulations may include various solvents to dissolve stain components including aqueous and organic solvents including but not limited to e.g., water and alcohols including but not limited to e.g., methanol, ethanol, isopropyl alcohol, etc.

The histological stains and components thereof include those commercially available from such suppliers including not limited to e.g., Sigma Aldrich, Thermo Fisher Scientific, Avantor Proformance Materials, VWR International, Polysciences Inc., and the like.

Subjects from which a specimen may be acquired include but are not limited to human subjects, mammalian subjects (e.g., primates (apes, gorillas, simians, baboons, orangutans, etc.), ungulates (e.g., equines, bovines, camelids, swine, etc.), canines, felines, rodents (mice, rats, etc.), etc. Specimens may include biological fluid samples and biological samples which may be processed prior to imaging, e.g., processed onto a slide and histologically stained. In instances where the specimen is a hematological sample (e.g., a blood sample) the sample may be processed into a smear and stained with a hematological stain. Suitable methods for processing a hematological sample include but are not limited to e.g., those described in U.S. Pat. Nos. 9,011,773 and 9,028,778; the disclosures of which are incorporated herein by reference.

Systems

The instant disclosure includes systems for assessing a histologically stained specimen. The systems of the instant disclosure involve components configured to perform the methods of determining color signatures from a histologically stained specimen and making an assessment based on the determined color signatures. Such systems may include image processing circuitry configured to perform one or more of the steps of the methods of color signature determination and/or specimen assessment as described herein. Such systems may include an image capture device for generating images of the specimen or may receive pre-captured images from a connected device.

The components of the instant systems may be assembled in a single device or may be assembled as a system of components separated between in two or more devices. In some instances, a device, a system or components thereof that performs the image processing functions may be external but near (i.e., attached to the external housing of or on the same working surface or within the same room or building, etc.) a image capture device and/or histology analyzer that processes the specimen and/or obtains the digital image and/or performs the primary histological analysis. In other instances, a device, a system or components thereof that perform the image processing functions may be positioned internally (i.e., within, inside of, or housed within) a histology analyzer that processes the specimen and/or obtains the digital image and/or performs the primary histological analysis.

Image Capture Devices

At a minimum a suitable image capturing device will include a digital color camera capable of capturing a digital image and a means of storing the digital color image and/or transferring the image to attached image processing circuitry or to an attached storage device for later transfer to image processing circuitry. Suitable digital color cameras will vary and will generally include any digital color camera (e.g., with one or more CCD or CMOS sensors) with sufficiently high resolution and sufficient color capture to capture an image that may be processed according to the methods described herein. Depending on the particular features used in a subject method suitable digital cameras may include a color camera with resolution ranging from less than about 0.3 megapixel to about 14.0 megapixel or more including but not limited to e.g., 0.3 megapixel or more, 0.9 megapixel or more, 1.3 megapixel or more, 1.4 megapixel or more, 2 megapixel or more, 3 megapixel or more, 3.3 megapixel or more, 5 megapixel or more, 7 megapixel or more, 10 megapixel or more, 12 megapixel or more, 14.0 megapixel or more, and the like.

Suitable digital color cameras include but are not limited to e.g., custom build digital color cameras, consumer grade digital color cameras (e.g., consumer grade digital color cameras converted for microscopic use) and those digital microscopy color cameras commercially available from various manufactures including but not limited to e.g., Dino-Eye, Dino-Lite, Jenoptik ProgRes, KoPa, Leica, Motic, Olympus, Omano, OptixCam, PixelLINK, Zeiss, etc.

In some instances, a digital color camera of the instant system may be attached to a microscope configured for manual or automated microscopy. Any suitable microscope may find use in the described systems provided the microscope is configured with sufficient optics and provides sufficient magnification to allow the capture of digital color images that can be processed according to the methods described herein. As such, microscope components of the instant systems include custom units, e.g., as assembled from individual microscope components, and commercially available units.

Suitable microscopes include but are not limited to e.g., those available from various manufactures including e.g., Bruker Optics (www(dot)brukeroptics(dot)com), Carl Zeiss (www(dot)zeiss(dot)com), CRAIC (www(dot)microspectra (dot)com), Edmund Optics (www(dot)edmundoptics(dot) com), FEI (www(dot)fei(dot)com), Hamamatsu (www(dot) hamamatsu(dot)com), Hirox-USA (www(dot)hirox-usa(dot) com), Hitachi High Technologies (www(dot)hitachi-hta (dot)com), JEOL (www(dot)jeol(dot)com), Keyence (www (dot)keyence(dot)com), Kramer (www(dot)kramerscientific (dot)com), Leica Microsystems (www(dot)leica(dot)com), Meiji Techno America (www(dot)meijitechno(dot)com), Motic Instruments (www(dot)motic(dot)com), Nikon Instruments (www(dot)nikoninstruments(dot)com), Ocean Optics (www(dot)oceanoptics(dot)com), Olympus (www(dot)olympusamerica(dot)com), OPTIKA Microscopes (www(dot)optikamicroscopes(dot)com), Phenom-World (www(dot)phenom-world(dot)com), Prior Scientific (www(dot)prior(dot)com), Warner (www(dot)warneronline(dot)com), and the like.

The instant microscopic systems may further include components for automated slide preparation, automated slide handling, automated imaging, automated scanning, and the like.

In some instances, a microscopic system of the instant disclosure may be encompassed within or connected, e.g., physically or electronically, to a histology analyzer, including e.g., an automated histology analyzer, an automated cytology analyzer, an automated hematological analyzer, etc.

Histology analyzers of the instant disclosure include but are not limited to e.g., those commercially available from Abbott Laboratories and/or Abbott Diagnostics (including e.g., the CELL-DYN systems, and the like), from Sysmex (including e.g., the Sysmex D160, CellaVision DM1200, and the CellaVision DM9600 systems and the like), from MEDICA (including e.g., the EasyCell systems, and the like), from Horiba (including e.g., the Pentra and Micros systems, and the like), from Siemens (including e.g., the ADVIA and Kematek systems, and the like), from Beckman Coulter (including e.g., the UniCel systems, and the like), etc.

Computer and Circuitry Components

In some instances, the components of the systems as described herein may be connected by a wired data connection. Any suitable and appropriate wired data connection may find use in connecting the components of histology stain assessment systems, e.g., as described herein, including but not limited to e.g., commercially available cables such as a USB cable, a coaxial cable, a serial cable, a C2G or Cat2 cable, a Cat5/Cat5e/Cat6/Cat6a cable, a Token Ring Cable (Cat4), a VGA cable, a HDMI cable, a RCA cable, an optical fiber cable, and the like. In some instances, e.g., where data security is less of a concern, wireless data connections may be employed including but not limited to e.g., radio frequency connections (e.g., PAN/LAN/MAN/WAN wireless networking, UHF radio connections, etc.), an infrared data transmission connection, wireless optical data connections, and the like.

In some instances, the systems of the instant disclosure include image processing circuitry. Such image processing circuitry may be programmed and/or contain instructions to perform one or more tasks related to processing a digital image received from an image capture device. For example, in some instances, the image processing circuitry is programmed to determine a ROI and/or a color signature, described above, from a digital image obtained from digital storage or generated by an image capture device. In some instances, the image processing circuitry is programmed to make a comparison between a determined color signature and a reference color signature, e.g., as stored in a library, to make an assessment according to the methods described herein.

In some instances, image processing circuitry may be programmed to perform one or more steps, in isolation or in combination, of the methods described herein including but not limited to e.g., obtaining a digital color image of the specimen, defining on the image a ROI, quantifying one or more color parameters, determining a color signature, etc. In addition, image processing circuitry may be programmed to perform one or more additional steps, in isolation or in combination, including but not limited to generating a mask of a digital image. In some instances, image processing circuitry may be further programmed to make a comparison between a determined color signature and a reference color signature, e.g., to perform an assessment of the histologically stained specimen, including e.g., one or more of the assessments described herein.

In addition to the direct image processing steps, image processing circuitry may be, or may have an operable connection with additional circuitry, configured to perform one or more additional functions including but not limited to e.g., receive a digital image from an image capture device, retrieve a digital image from memory, retrieve a reference value from memory, store a processed image to memory, store a value quantified from an image to memory, store the result of a comparison to memory, etc.

In some instances, the systems as described herein further include a signal system where the signal system may be configured to report the result of a comparison or assessment. Such signal systems will vary depending on the particular configuration of the device and or system and may include but are not limited to e.g., an alarm, an indicator light, a display (e.g., a computer monitor, a graphical user interface (GUI), etc.), a printer configured to print, e.g., onto tangible media (including e.g., paper or tape), and the like. In some instances, the signal system indicates, e.g., sounds, lights up, or otherwise displays, to a user whether a histological stain is adequate or inadequate.

In some instances, the signal system indicates, e.g., sounds, lights up, or otherwise displays, to a user the quality of the histological stain. For example, in some instances, the system may include a display configured to report a result of one or more assessments generated according to the methods described herein. In some instances, the system may transmit the result to a remote display or transmit the result as data (e.g., transmit to a data store, transmit to a user via electronic means (e.g., email), etc.). In some instances, a system may report the histological stain assessment as part of a larger report, e.g., as part of a cell count or complete hematological report.

The image processing circuitry is specifically configured or programmed to perform the functions according to the methods as described herein, including color parameter quantification functions, color signature determination functions, and comparison tasks, and may include at least one data processing unit for performing data related functions.

By "data processing unit", as used herein, is meant any hardware and/or software combination that will perform the functions required of it. For example, any data processing unit herein may be a programmable digital microprocessor such as available in the form of an electronic controller, mainframe, server or personal computer (desktop or portable). Where the data processing unit is programmable, suitable programming can be communicated from a remote location to the data processing unit, or previously saved in a computer program product (such as a portable or fixed computer readable storage medium, whether magnetic, optical or solid state device based).

Substantially any circuitry can be configured to a functional arrangement within the devices and systems for performing the methods disclosed herein. The hardware architecture of such circuitry, including e.g., a specifically configured computer, is well known by a person skilled in the art, and can comprise hardware components including one or more processors (CPU), a random-access memory (RAM), a read-only memory (ROM), an internal or external data storage medium (e.g., hard disk drive). Such circuitry can also comprise one or more graphic boards for processing and outputting graphical information to display means. The above components can be suitably interconnected via a bus within the circuitry, e.g., inside a specific-use computer. The circuitry can further comprise suitable interfaces for communicating with general-purpose external components such as a monitor, keyboard, mouse, network, etc. In some embodiments, the circuitry can be capable of parallel processing or can be part of a network configured for parallel or distributive computing to increase the processing power for the present methods and programs. In some embodiments, the program code read out from the storage medium can be written into a memory provided in an expanded board inserted in the circuitry, or an expanded unit connected to the circuitry, and a CPU or the like provided in the expanded board or expanded unit can actually perform a part or all of the operations according to the instructions of the programming, so as to accomplish the functions described.

The systems of the instant disclosure may further include a "memory" that is capable of storing information such that it is accessible and retrievable at a later date by a computer. Any convenient data storage structure may be chosen, based on the means used to access the stored information. In certain aspects, the information may be stored in a "permanent memory" (i.e. memory that is not erased by termination of the electrical supply to a computer or processor) or "non-permanent memory". Computer hard-drive, CD-ROM, floppy disk, portable flash drive and DVD are all examples of permanent memory. Random Access Memory (RAM) is an example of non-permanent memory. A file in permanent memory may be editable and re-writable.

In some instances, the system may include a memory containing reference color signatures for making the comparisons of the assessments as described herein. For example, in some instances a memory of the instant system may include one or more color signature reference target values, one or more color signature reference ranges, one or more color signature reference thresholds, and combinations thereof.

In addition to the components of the devices and systems of the instant disclosure, e.g., as described above, systems of the disclosure may include a number of additional components, such as data output devices, e.g., monitors and/or speakers, data input devices, e.g., interface ports, keyboards, etc., fluid handling components, slide handling components, power sources, etc.

Computer Readable Medium

The instant disclosure includes computer readable medium, including non-transitory computer readable medium, which stores instructions for assessing a histologically stained specimen based on a determined color signature from a digital image of the histologically stained specimen. Aspects of the instant disclosure include computer readable medium storing instructions that, when executed by a computing device, cause the computing device to perform one or more of the steps of defining an ROI on a digital color image of a histologically stained specimen, quantifying color parameters from a digital color image of a histologically stained specimen, determining a color signature of a histologically stained specimen, comparing a determined color signature to a reference color signature to assess a histologically stained specimen.

In some instances, a computer readable medium of the instant disclosure stores instructions that cause a computing device to make an assessment, e.g., a histological stain adequacy assessment, a histological stain quality assessment, etc., based on a comparison of a color signature determined from a digital color image of the specimen and reference color signature stored in a library on the computer readable medium. In some instances, a library of reference color signatures may be specific for a particular category of histological stains, e.g., a computer readable medium may store a library of reference color signatures specifically for hematological stains, e.g., Romanowsky stains, etc.

In some instances, a computer readable medium of the instant disclosure stores only a library of reference color signatures as described herein. In other instances, a computer readable medium of the instant disclosure stores at least both instructions that cause a computing device to perform one or more of the steps according to the methods as described herein and a library of reference color signatures. In some instances, a computer readable medium storing both instructions that cause a computing device to perform one or more of the steps according to the methods as described herein and a library of reference color signatures is specific for hematological stains, e.g., Romanowsky stains, etc.

In certain embodiments, instructions in accordance with the methods described herein can be coded onto a computer-readable medium in the form of "programming", where the term "computer readable medium" as used herein refers to any storage or transmission medium that participates in providing instructions and/or data to a computer for execution and/or processing. Examples of storage media include a floppy disk, hard disk, optical disk, magneto-optical disk, CD-ROM, CD-R, magnetic tape, non-volatile memory card, ROM, DVD-ROM, Blue-ray disk, solid state disk, and network attached storage (NAS), whether or not such devices are internal or external to the computer. A file containing information can be "stored" on computer readable medium, where "storing" means recording information such that it is accessible and retrievable at a later date by a computer.

The computer-implemented method described herein can be executed using programming that can be written in one or more of any number of computer programming languages. Such languages include, for example, Java (Sun Microsystems, Inc., Santa Clara, Calif.), Visual Basic (Microsoft Corp., Redmond, Wash.), and C++ (AT&T Corp., Bedminster, N.J.), as well as any many others.

The following examples are offered by way of illustration and not by way of limitation.

EXAMPLES

Example 1: Method of Assessing Coloration Patterns in a Romanowsky Type Stained Specimen Using a Set of 6 Color Parameters (i.e., "Coloration Coefficients Method")

The method used digital images from a Romanowsky-type stained hematological specimen smear, obtained from an optical microscope equipped with a color charge-coupled device (CCD) camera in Red, Green, and Blue (RGB) format. For each pixel, 3 color parameters (8 bit digitized values of cumulative absorbance in red, green and blue spectral channels) were measured and 3 color coefficients (a Red Coefficient, a Blue Coefficient and a Blue-Red Balance) were calculated to characterize hue and intensity of the color for any given pixel in the image. A Red Coefficient was calculated as a ratio of mean intensity value in the red channel versus the green channel, a Blue Coefficient was calculated as a ratio of mean intensity value in the blue channel versus the red channel, while a Blue-Red Balance was a ratio of the Blue Coefficient versus the Red Coefficient.

These coefficients were strategically devised to characterize Romanowsky-type stains. The scientific principle behind this method harnesses a concept of complementary colors and is based on the absorbance spectra of Romanowsky-type stains. A Romanowsky-type stain reagent typically consists of two main dyes (eosin and azure/methylene blue), their derivatives and supplementary additives. An absorbance spectrum of the Romanowsky stain normally has two main absorbance bands with peaks positioned at $\lambda$ ~520 nm and $\lambda$ ~650 nm corresponding to eosin and azure/methylene blue, respectively (FIG. 1).

When a specimen absorbs white light in the red range of the optical spectrum, $\lambda$ ~650 nm, the resulting light coming off the specimen will be depleted from the red photons and produces a blue color with its hues. Similarly, when a specimen absorbs white light in the green range of the spectrum, $\lambda$ ~520 nm, the resulting light coming off the specimen will be depleted from the green photons and produces a red color and its hues. For the areas in the specimens which contain both dye molecules in different amounts, a combination of differential absorbance at $\lambda$ ~520 nm and $\lambda$ ~650 nm produces a purple color and its hues. Depending on the molecular composition, different intracellular compartments will be stained in blue, red, purple colors and their various hues (for a more detailed explanation of the typical colors/hues found in the blood cells stained with Romanowsky stains, see, Brown, Hematology Principles and Procedures, 6th ed., 1993. Lea and Febiger, Philadelphia, p. 102-105; Carr and Rodak, Clinical Hematology Atlas, 3rd Ed., 2009. Saunders Elsevier).

Figure 2:
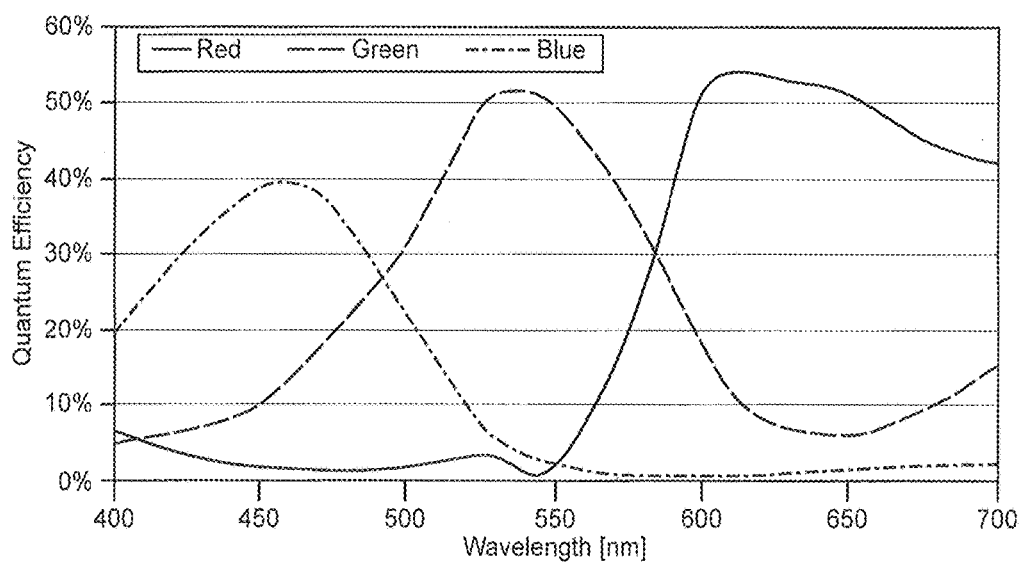
FIG. 2 depicts an example of a spectral response for a color CCD camera.

When a stained blood smear was examined using the digital optical microscope, a color CCD detector (with three channels, Red, Green and Blue, RGB) recorded different signals in accordance to the spectral absorption of the specimen. Each color channel (R, G and B) has different sensitivities in different spectral ranges as shown in FIG. 2. When a specimen absorbs white light in the green spectral range, $\lambda$ ~520 nm, the signal in the green channel will be low due to the absorbance, while a signal in the red channel will be higher.

Therefore, an intensity value in the red channel, R, characterizes the intensity of the red color in the specimen (dark or light red), while a ratio of red intensity value over the green intensity value, G (comprising a Red Coefficient in this method), quantifies the hue of the red color: Red Coefficient=Red signal/Green signal.

Similarly, an intensity value in the blue channel, B, characterizes the intensity of the blue color in the specimen (dark or light blue), while a ratio of blue intensity value over the red intensity value, R, (comprising a Blue Coefficient in this method) quantifies the hue of the blue color: Blue Coefficient=Blue signal/Red signal.

A ratio of Blue Coefficient over Red Coefficient provides a measure of the balance between two key spectral ranges (blue and red), and respectively quantifies a purple hue: Blue-Red Balance=Blue Coefficient/Red Coefficient.

FIG. 1: Examples of absorption spectra for two types of Romanowsky stains, Wright Giemsa and May Grunwald, with main absorbance bands positions at $\lambda$ ~520 nm and $\lambda$ ~650 nm.

FIG. 2: Example of a spectral response for a color CCD camera.

Figure 3A:
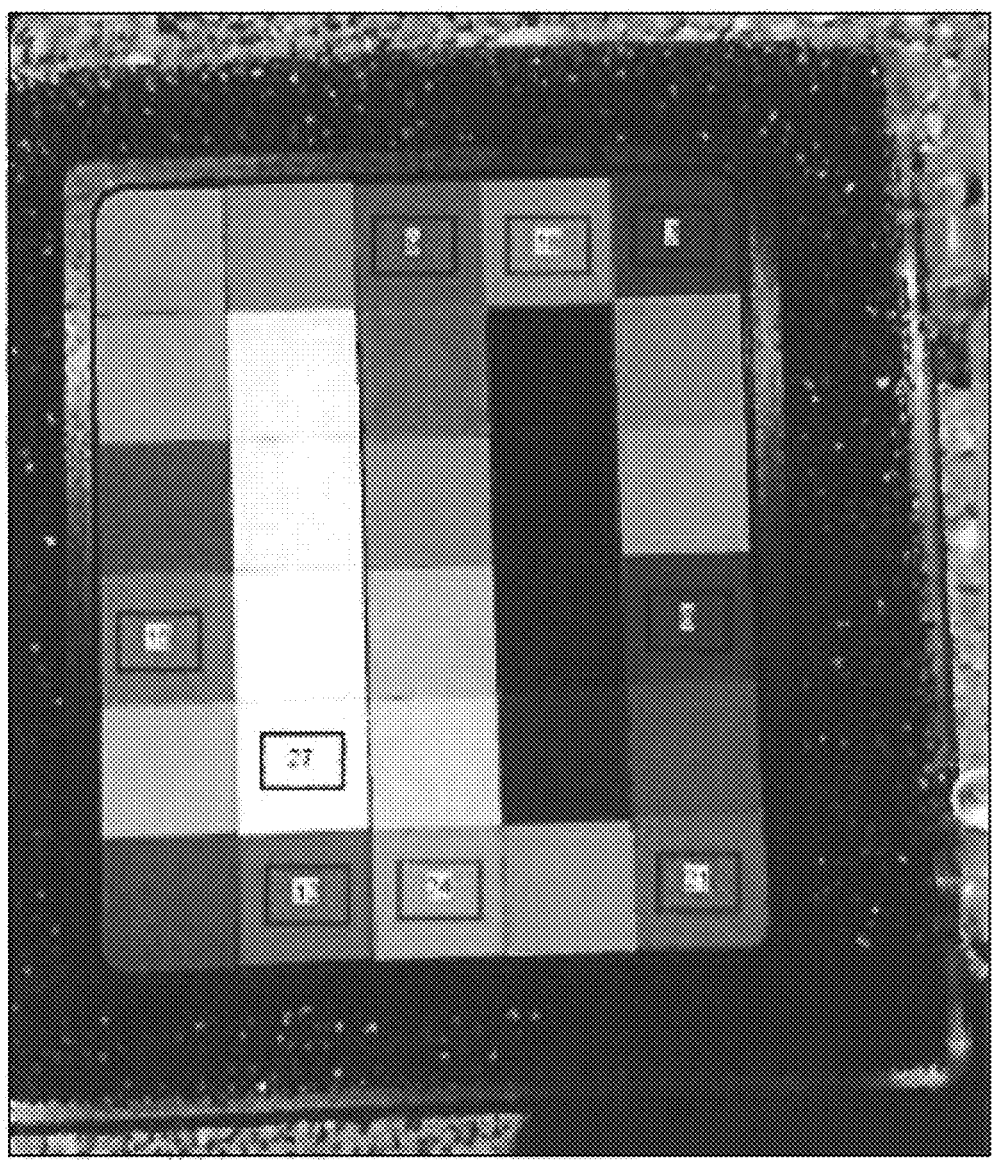
FIGS. 3A and 3B depicts a color target mask with well-defined colors (FIG. 3A), and a table illustrating the set of color features calculated for the target mask (FIG. 3B).

Example 2: Testing of "Coloration Coefficients Method" Using a Color Calibration Target with a Well-Defined Color Mask A concept of the present method was tested by using a color calibration target with a well-defined color mask (FIG. 3A). The data calculated for various hues of red, blue and purple colors on the mask (FIG. 3B) validate the concept of the method. For example, a Blue Coefficient obtained for blue colors was significantly higher compared to non-blue colors, while a darker versus lighter blue color is discriminated by a mean value of a blue signal. Similarly, reddish colors have a higher value of Red Coefficient, with a varying intensity of red signal depending on the lightness or darkness of the red color. Additional information on the ratio (balance) of red and blue hues in the specific color was given by the Blue-Red Balance, which respectively showed high values for blue colors, low values for red colors and around a unit value for hues of purple.

Figure 3B:
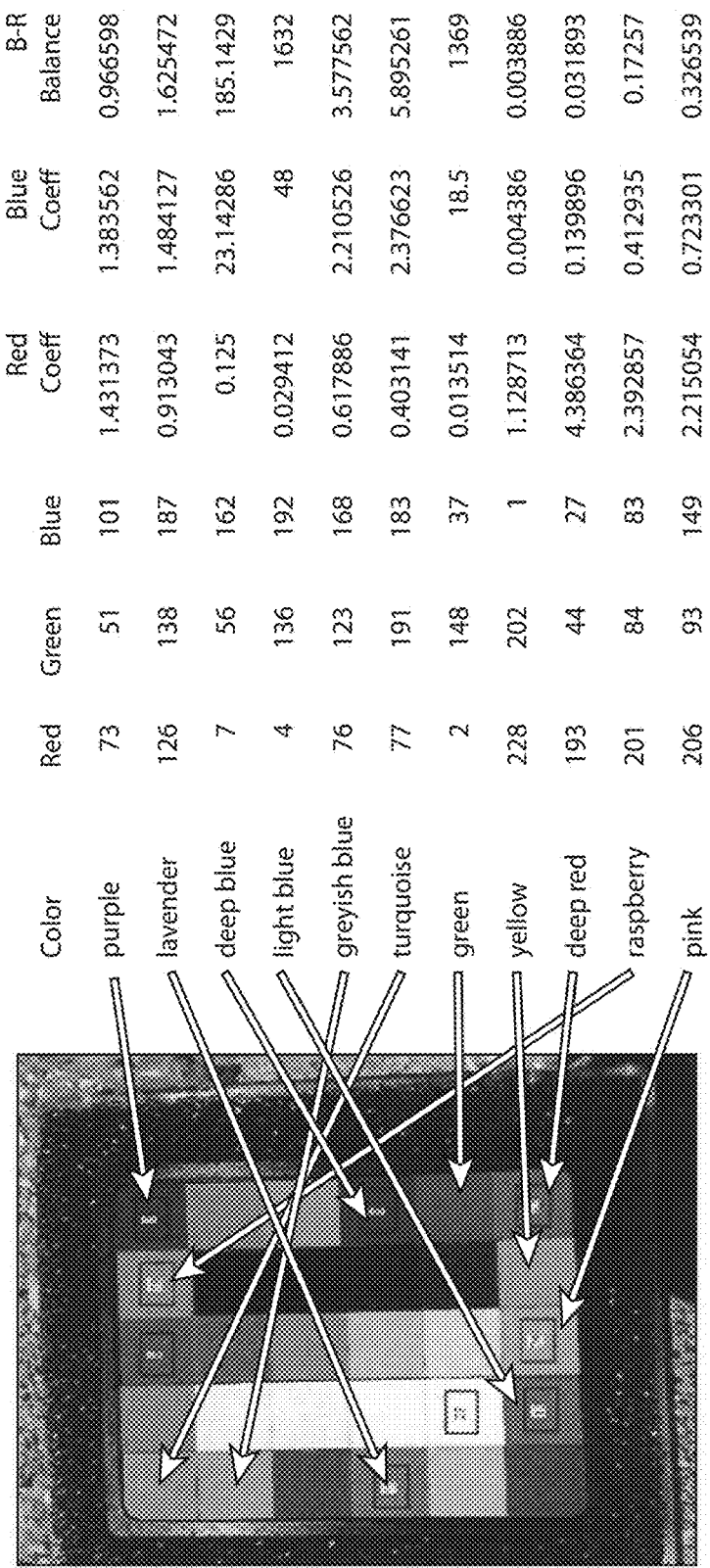

FIG. 3: A color target mask with well-defined colors manufactured in accordance with the International Commission on Illumination (CIE) chromaticity diagram (FIG. 3A), and a set of color features calculated for the target mask (FIG. 3B).

Example 3: Assessment of the Coloration of Eosinophils and Red Blood Cells Using "Coloration Coefficients Method"

This example demonstrates how the present method was applied to evaluate coloration of eosinophils and red blood cells in different smears stained with a Wright-Giemsa stain. As seen from the data provided, a pale eosinophil cell is clearly discriminated from a darker eosinophil cell by having higher values of R, G, B signals, while more reddish (for the granules) or more bluish (for the nuclei) hues for each main color can be distinguished by varying values of color coefficients (FIG. 4). Similarly, a normal erythrocyte can be discriminated from the erythrocyte with polychromasia by the value of the Blue-Red Balance, which indicates that a polychromatic cell has a higher degree of blue hue than the normal cell, with Blue-Red Balance values 1.03 (polychromatic) versus 0.85 (normal) (FIG. 5).

FIG. 4: Application of the present method to evaluate eosinophil coloration images of Wright-Giemsa stained smears (FIG. 4A), and the set of color features calculated (separately for granules and nuclei) for two different eosinophils (FIG. 4B).

Figures 5A, 5B:
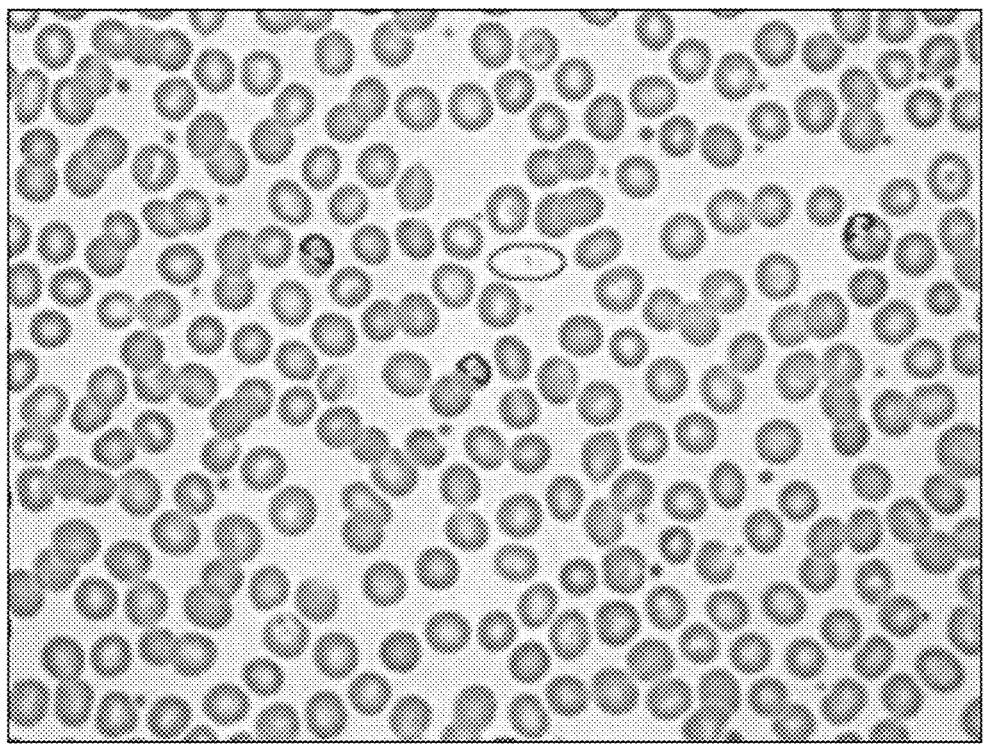
FIGS. 5A and 5B depicts the evaluation of erythrocyte coloration in an image of a Wright-Giemsa stained smear.

FIG. 5: Application of the present method to evaluate erythrocyte coloration in an image of a Wright-Giemsa stained smear (FIG. 5A), and the set of color features calculated for normal and polychromatic erythrocytes (FIG. 5B).

Example 4: Calibration of Illumination Source of the Digital Microscope for Coloration Measurement Using a Blank-Slide Normalization Images of a blank slide were taken to standardize a digital microscope for coloration measurement of cells. The images of a blank slide were used to calculate mean RGB values and 3 Color Coefficients. In this way, spectral range and brightness level of illumination in the object plane of the microscope as well as a color balance of the CCD camera were quantified. The studies indicate that measurement of cell coloration in the same specimen can be related among different microscopes through the use of blank slide normalization.

Table 1 demonstrates that, depending on the light source used in the microscope, the images of the blank slide taken with the same microscope optics and CCD detector (24 bit RGB, 8 bit/color) display slightly different color balance and brightness.

TABLE 1

| Illumination | Color | Red | Green | Blue | Red Coeff | Blue Coeff | B-R Balance |
|---|---|---|---|---|---|---|---|
| Light source1 | Blank slide | 240 | 250 | 237 | 0.96 | 0.9875 | 1.02864583 |
| Light source2 | Blank slide | 245 | 246 | 245 | 0.995935 | 1 | 1.00408163 |
| Light source3 | Blank slide | 221 | 231 | 223 | 0.95671 | 1.00905 | 1.05470813 |

Through the use of a blank-slide calibration, a quantitative link was established between the spectral illumination range of the light source used in the microscope and the coloration pattern it produces in the image (Note: blank slide calibration is performed using the same detector (e.g., a color CCD camera) as used for specimen imaging).

Example 5: Quantitative Link Between Spectral Absorbance of Romanowsky Stain and Coloration Pattern it Produces in the Specimen Using "Coloration Coefficient Method"

This example demonstrates how the "coloration coefficient method" can link absorbance spectrum of the stain to the cell coloration it produces in the stained blood smears (using a particular pre-defined staining protocol) via calculation of 6 Color Parameters (3 mean RGB values and 3 Color Coefficients). In this way, the impact of even slight changes in the chemical formulation or processes used in formulating the stain can be quantitatively referenced to changes in the cell coloration.

Blood smears prepared from the same blood specimen were stained with two slightly different formulations of the Wright-Giemsa stain.

Figure 6:
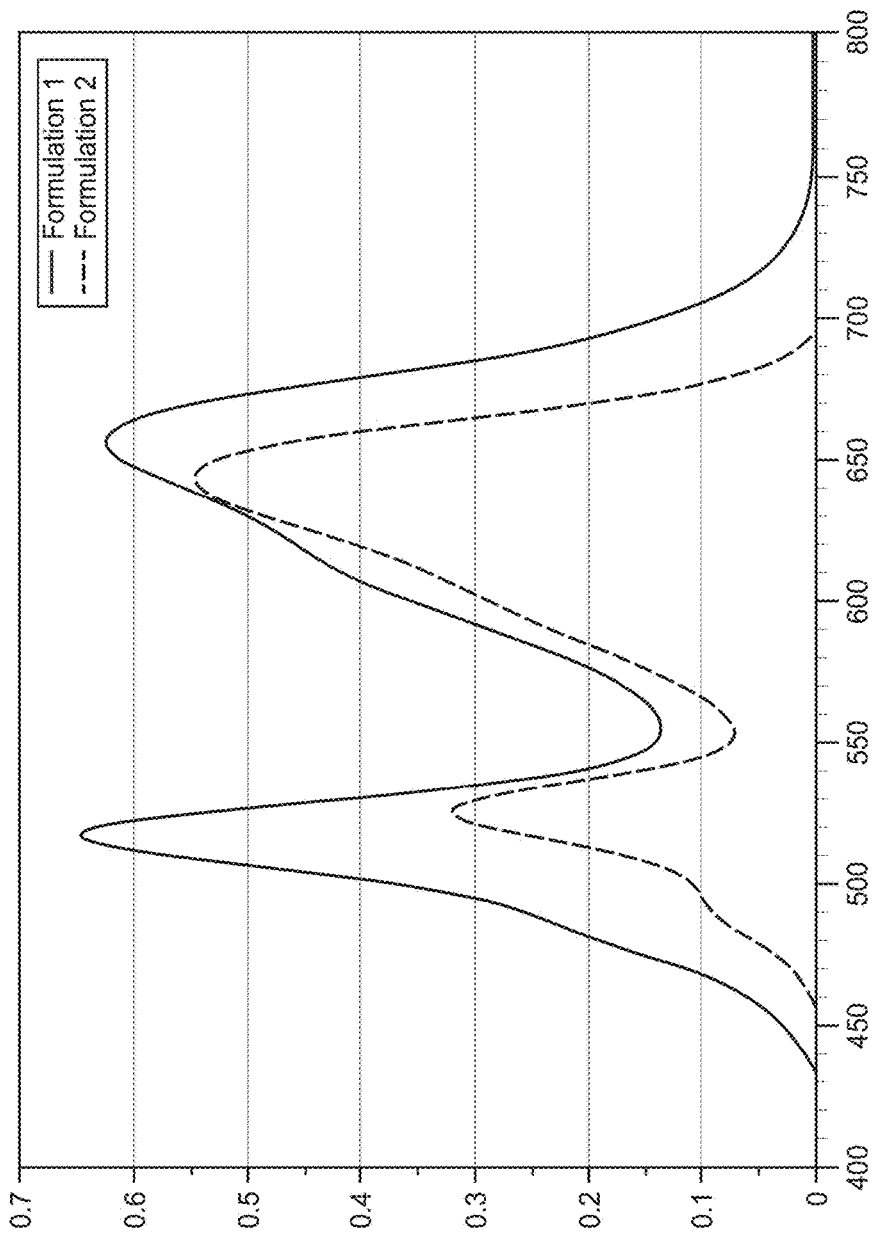
FIG. 6 provides the absorbance spectra of two different formulations of Wright-Giemsa stain used for staining blood smears with the same staining protocol.

The absorbance spectra of two stain formulations used in the test are provided in FIG. 6. Notably, the main absorbance peaks for two different stain formulations not only differ by their amplitudes (reflects on concentration of dyes molecules), but also by spectral position of the peak wavelengths which reflects on chemical modification of dyes molecules. Images of two basophil cells (FIG. 7) selected from the smears stained with dye formulations 1 and 2 (using the same staining protocol) indicated that cells stained with different formulations exhibit slightly different hues of blue, red and especially purple, even if the intensity of the coloration (dark or light) can be similar. Importantly, analysis of the values of Blue-Red Balance indicated that basophil 2 has more purple coloration, while basophil 1 was mostly blue, with Blue-Red Balance values respectively 1.27 (nuclear material) and 1.45 (granular material) for basophil 2 and 2.25 (nuclear material) and 2.63 (granular material) for basophil 1.

FIG. 6. Absorbance spectra of two different formulations of Wright-Giemsa stain used for staining blood smears with the same staining protocol.

Figure 7:
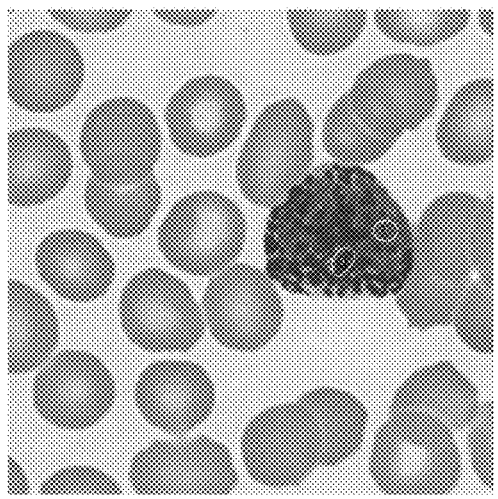
FIG. 7 provides images of basophil cells (from the same blood specimen) acquired on slides stained with slightly different formulations of Wright-Giemsa stain, (left) stain formulation 1 and (right) stain formulation 2.
Figure 7:
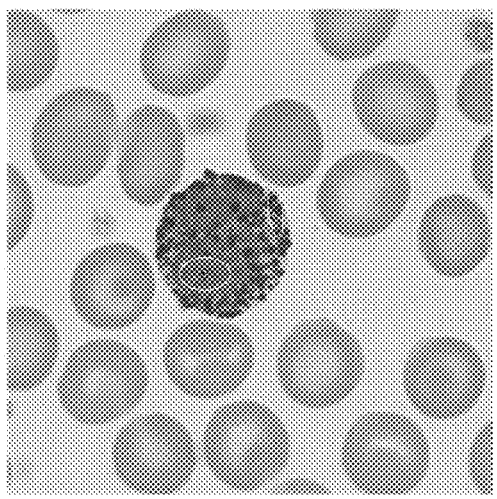

FIG. 7. Images of two basophil cells (from the same blood specimen) acquired on slides stained with slightly different formulations of Wright-Giemsa stain, (a) stain 1; (b) stain 2.

Data were acquired on the same microscope, using the same light source and CCD camera.

Example 6: Calculations from Stained Slide Specimens for Characterizing Coloration Quality A slide containing a stained specimen to be analyzed was placed under a microscope connected to a digital camera. Computer algorithms were applied to locate stained cells and other specimen elements in the stained specimen and images were captured. Algorithms were then used to extract color features from cellular and sub-cellular elements in the sample that characterized the stain attributes, for example, mean values for Red, Green and Blue channels, their optical density, hue, lightness, saturation, or their respective Red/Blue, Blue/Green, Green/Red ratios. Additionally, several calculations were used to characterize coloration quality, including the vectors that characterize the colors of cell nuclei and cytoplasm for each individual cell type or the ratios of such, which are described as follows:

$CSCV_{rgb} = \sqrt{(Mean_{red})^2 + (Mean_{green})^2 + (Mean_{blue})^2}$, wherein "Mean" represents the mean intensity value for each color channel over a ROI of the digital image comprising the cytoplasm of a cell or a portion thereof;

$CSCV_{hsl} = \sqrt{(Mean_{hue})^2 + (Mean_{saturation})^2 + (Mean_{luminosity})^2}$, wherein "Mean" represents the mean hue, saturation and luminosity values over a ROI of the digital image comprising the cytoplasm of a cell or a portion thereof, $NSCV_{rgb} = \sqrt{(Mean_{red})^2 + (Mean_{green})^2 + (Mean_{blue})^2}$, wherein "Mean" represents the mean intensity value for each color channel over a ROI of the digital image comprising the nucleus of a cell or a portion thereof;

$NSCV_{hsl} = \sqrt{(Mean_{hue})^2 + (Mean_{saturation})^2 + (Mean_{luminosity})^2}$, wherein "Mean" represents the mean hue, saturation and luminosity values over a ROI of the digital image comprising the nucleus of a cell or a portion thereof;

$NSCV_{rgb}$=Nuclear Stain Color Vector based on values in Red, Green and Blue channels; $CSCV_{rgb}$=Cytoplasmic Stain Color Vector based on values in Red, Green and Blue channels; $NSCV_{hsl}$=Nuclear Stain Color Vector depicted by their hue, saturation and luminosity values; $CSCV_{hsl}$=Cytoplasmic Stain Color Vector depicted by their hue, saturation and luminosity values.

This information was then used to characterize stains and establish threshold criteria according to whether or not the stained specimens are considered acceptable for clinical, instrument or research use. The specimen characteristics were interrogated against those thresholds to determine whether the stain quality was acceptable or not, and to determine usability.

Example 7: Calculations from Digital Images of Stained Specimens for Machine Learning and Coloration Quality Assessments A database of training images is pre-collected, comprised of images of cells of known acceptable and unacceptable stain quality as determined by qualified professionals. These images are processed for cell segmentation into various ROIs. Algorithms are applied to extract signature color features from cellular and sub-cellular elements in the images which characterize their stain attributes, that include but are not limited to mean values for Red, Green and Blue channels, their optical density, hue, lightness, saturation, or their respective Red/Blue, Blue/Green, Green/Red ratios. These values describe the signature color of the chosen ROIs for a given image for each specimen. Based on the extracted feature parameters and the classification given by trained professionals, a pre-trained classifier is developed using a Support Vector Machine (SVM) classification algorithm or the like, that is capable of classifying stain quality accordingly.

Figure 8:
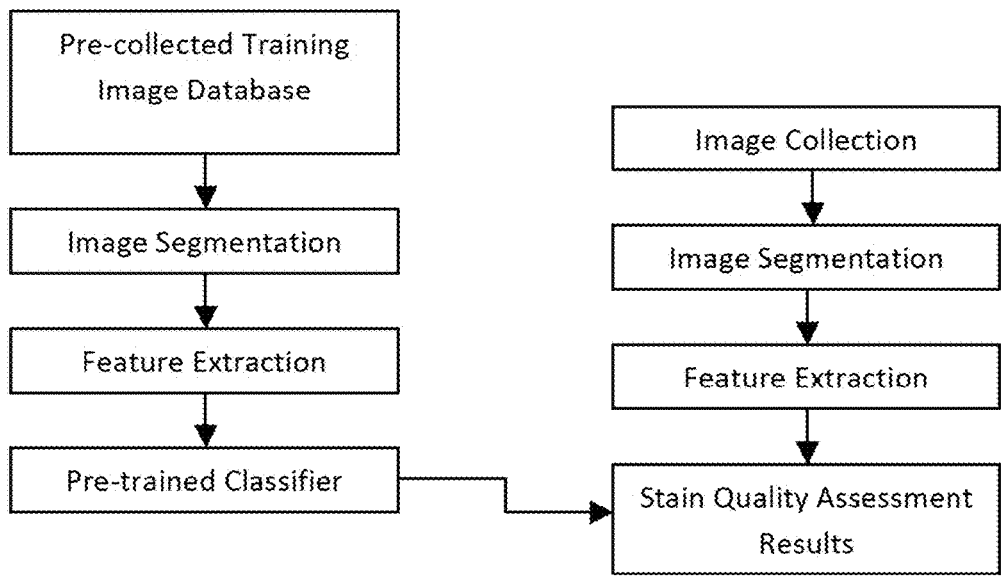
FIG. 8 provides a flow chart depicting computer training and specimen assessment according to an embodiment of the instant disclosure.

Then, a slide containing a stained specimen to be analyzed is placed under a microscope connected to a camera. Computer algorithms are applied to locate stained cells or other specimen elements and segment them into the desired ROIs. These are then processed using the pre-trained classifier and the quality of the stain is automatically determined (see FIG. 8).

This methodology can be used to characterize and assess stain quality of various different aspects of interest. For example, stain quality of single cell populations (e.g. stain quality of the lymphocyte cell population, etc.) on a smear, or their cell compartments (e.g. stain quality of the cytoplasm of all neutrophils on a smear, etc.), or multiple cell populations combined (e.g. overall stain quality including all cell populations on a smear, and therefore of a stain quality of the whole stained smear) can be assessed.

To illustrate this concept, cell images of a faintly stained lymphocyte and a deeply stained lymphocyte were used. The cells on the images were segmented into different ROIs: a nuclei ROI, and whole cell ROI, cytoplasm was contained between the nuclei ROI and the whole cell ROI. The red, green and blue channels mean values for the nucleus ROI of each cell were measured (see Table 2).

TABLE 2

|  | Faintly Stained Lymphocyte | Deeply Stained Lymphocyte |
| --- | --- | --- |
| Red Channel mean value | 94 | 65 |
| Green Channel mean value | 125 | 58 |
| Blue Channel mean value | 208 | 140 |

These signature color values contain the information pertaining to the signature color of each cell nucleus. This information can be represented in many ways to characterize the coloration of each of these ROIs. For example, these can be interconverted to other values like HSV, HSL, or Hexadecimal notation that describe them, and used in combination to represent the mean color of the chosen ROI. A visualization of the descriptive color representative of the nucleus in each case of the example above (derived from the signature color values related to the color on a reference color table) can be seen by inputting the numeric color values (e.g., as presented in Table 3 below) into a color converter or color generator (e.g., as available through various online or offline utilities including but not limited to e.g., at http(colon)//rapidtables(dot)com/convert/color/index(dot)htm).

TABLE 3

| Hex (#) | Faintly Stained Nucleus 5E7DD0 | | | Deeply Stained Nucleus 413A8C | | |
| --- | --- | --- | --- | --- | --- | --- |
| RGB (R, G, B) | 94 | 125 | 208 | 65 | 58 | 140 |
| HSV (H, S, V) | 224 | 55 | 82 | 245 | 59 | 55 |
| HSL (H, S, L) | 224 | 55 | 59 | 245 | 41 | 39 |

Figure 9:
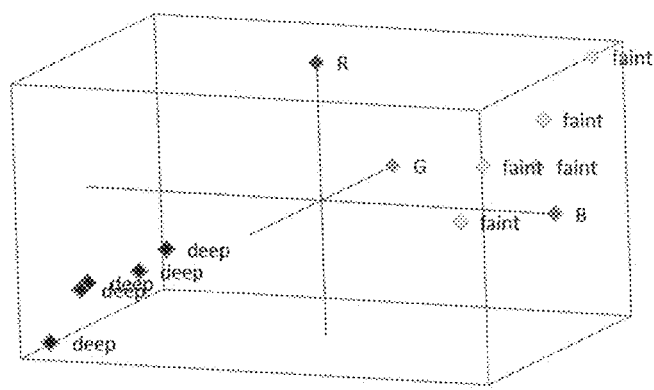
FIG. 9 provides a scatter-pot of RGB signature values collected from faintly stained and deeply stained lymphocytes according to an embodiment of the instant disclosure.

As an example, images of various lymphocytes from different specimens stained with faint stain or deep stain were analyzed to obtain the RBG signature colors values for their nuclei (Table 4), and the corresponding RGB signature values were plotted as 3D scatter (FIG. 9).

TABLE 4

| Stain type | Lymphocyte nucleus | R | G | B |
| --- | --- | --- | --- | --- |
| faint | 1 | 94 | 125 | 208 |
| faint | 2 | 106 | 136 | 207 |
| faint | 3 | 79 | 110 | 197 |
| faint | 4 | 94 | 121 | 199 |
| faint | 5 | 123 | 150 | 213 |
| deep | 6 | 65 | 58 | 140 |
| deep | 7 | 48 | 48 | 135 |
| deep | 8 | 74 | 69 | 152 |
| deep | 9 | 68 | 64 | 148 |
| deep | 10 | 63 | 56 | 139 |

From FIG. 9 it is evident that the two stains tend to cluster onto distinct spatial locations, thus illustrating how a SVM algorithm could similarly categorize and separate clusters. Then, when new smears images of unknown stain quality are processed, the classifier algorithm could classify the smear color quality by using its signature feature values to determine to which cluster it best fits. Thus the quality of the stain may be determined.

In addition to using the signature color values separately or in combination, it may also be converted to other single or other multiple values that would represent the signature color value for the selected cell ROI. These signature color values, in whichever form may be represented, can be used as extractable features. For example, features could be expressed as vectors representative of the signature color, or the ratios of such. For instance, the individual RBG signature color values for a particular ROI may be described by the angle and magnitude of its resultant vector as follows:

$$NSCV_{rgb} = \sqrt{(Mean_{red})^2 + (Mean_{green})^2 + (Mean_{blue})^2}$$

$$\beta_{NSCV_{rgb}} = \cos^{-1}(Mean_{blue}/NSCV_{rgb})$$

$$\theta_{NSCV_{rgb}} = (\cos^{-1}(Mean_{red}))\sqrt{(Mean_{red})^2 + (Mean_{green})^2}$$

$$CSCV_{rgb} = \sqrt{(Mean_{red})^2 + (Mean_{green})^2 + (Mean_{blue})^2}$$

$$\beta_{CSCV_{rgb}} = \cos^{-1}(Mean_{blue}/CSCV_{rgb})$$

$$\theta_{CSCV_{rgb}} = (\cos^{-1}(Mean_{red}))\sqrt{(Mean_{red})^2 + (Mean_{green})^2}$$

$$NSCV_{hsl} = \sqrt{(Mean_{hue})^2 + (Mean_{saturation})^2 + (Mean_{lightness})^2}$$

$$\beta_{NSCV_{hsl}} = \cos^{-1}(Mean_{lightness}/NSCV_{hsl})$$

$$\theta_{NSCV_{hsl}} = (\cos^{-1}(Mean_{hue}))\sqrt{(Mean_{hue})^2 + (Mean_{saturation})^2}$$

$$CSCV_{hsl} = \sqrt{(Mean_{hue})^2 + (Mean_{saturation})^2 + (Mean_{lightness})^2}$$

$$\beta_{CSCV_{hsl}} = \cos^{-1}(\text{Mean}_{lightness}/CSCV_{hsl})$$

$$\theta_{CSCV_{hsl}} = \frac{(\cos^{-1}(\text{Mean}_{hue}))}{\sqrt{(\text{Mean}_{hue})^2 + (\text{Mean}_{saturation})^2}}$$

$NSCV_{rgb}$=Nuclear Stain Color Vector based on values in Red, Green and Blue channels; $CSCV_{rgb}$=Cytoplasmic Stain Color Vector based on values in Red, Green and Blue channels; $NSCV_{hsl}$=Nuclear Stain Color Vector depicted by their hue, saturation and luminosity values; $CSCV_{hsl}$=Cytoplasmic Stain Color Vector depicted by their hue, saturation and luminosity values. β and θ describe the direction of a vector in 3D space.

Similarly, any other representation of these values, including voxels or the like could also be used to represent the signature color values and as extractable features.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method of assessing a histologically stained specimen, the method comprising:
   a) obtaining a digital color image of the specimen;
   b) defining on the image a region of interest (ROI) based on a biological feature of the specimen;
   c) separating the digital color image into individual color channels;
   d) determining a color signature for the ROI, wherein the color signature comprises:
      a mean intensity for a first color channel, a second color channel, and a third color channel;
      a first color coefficient calculated by determining the ratio of the mean intensity value for the first color channel to the mean intensity value for the second color channel;
      a second color coefficient calculated by determining the ratio of the mean intensity value for the third color channel to the mean intensity for the first or the second color channel; and
      a third color coefficient calculated by determining the ratio of the first color coefficient to the second color coefficient; and
   e) comparing the determined color signature to a reference color signature that is specific to the biological feature and the histological stain to assess the histologically stained specimen.

2. The method of claim 1, wherein the separating is performed after defining the ROI.

3. The method of claim 1, wherein the ROI comprises a cell or a portion thereof.

4. The method of claim 1, wherein the ROI comprises a plurality of cells.

5. The method of claim 1, wherein the ROI is the cytoplasm of a cell or a portion thereof.

6. The method of claim 1, wherein the ROI is the nucleus of a cell or a portion thereof.

7. The method of claim 1, wherein the reference color signature is derived from a reference histologically stained specimen.

8. The method of claim 1, wherein the reference color signature comprises a threshold value.

9. The method of claim 1, wherein the assessment comprises establishing whether the determined color signature is within a predetermined range and, when within the range, the specimen is further processed.

10. The method of claim 1, wherein the assessment comprises establishing whether the determined color signature is outside of a predetermined range and, when outside the range, the specimen is not further processed.

11. The method of claim 1, wherein the assessment is an evaluation of histological stain quality.

12. The method of claim 1, wherein the assessment is used in identifying the ROI as a feature of the image.

13. The method of claim 1, wherein the assessment is used in differentiating the ROI from other features of the image.

14. The method of claim 1, wherein the method further comprises quantifying additional ROIs of the image having a substantially similar color signature.

15. The method of claim 1, wherein the histological specimen is stained with a Romanowsky stain.

16. The method of claim 1, wherein the first color coefficient is calculated by determining the ratio of the mean intensity value for a red color channel to the mean intensity value for a green color channel.

17. The method of claim 1, wherein the second color coefficient is calculated by determining the ratio of the mean intensity value for a blue color channel to the mean intensity value for a red color channel.

18. The method of claim 1, wherein the first color coefficient is calculated by determining the ratio of the mean intensity value for a red color channel to the mean intensity value for a green color channel and the second color coefficient is calculated by determining the ratio of the mean intensity value for a blue color channel to the mean intensity value for a red color channel.

19. The method of claim 18, wherein the third color coefficient is calculated by determining the ratio of the first color coefficient to the second color coefficient.

20. The method of claim 1, wherein the histological specimen is derived from a biological sample selected from the group consisting of: a blood sample, a bodily fluid sample and a tissue sample.

21. The method of claim 1, wherein the biological feature is a cell, wherein the cell is selected from the group consisting of: an erythrocyte, a mast cell, a megakaryocyte, a basophil, a neutrophil, an eosinophil, a macrophage, a NK cell, a T cell, a B cell and a blood cell progenitor.

22. The method of claim 1, wherein the method further comprises calibrating an illumination source used in obtaining the digital color image, wherein calibrating comprises quantification of one or more color parameters over an ROI defined on a blank slide.

* * * * *